United States Patent
Shen et al.

(10) Patent No.: US 12,156,931 B2
(45) Date of Patent: Dec. 3, 2024

(54) ORGANIC COUNTERANION CO-ASSEMBLY STRATEGY FOR THE FORMATION OF CYCLODEXTRIN-CONTAINING HYBRID FRAMEWORKS

(71) Applicant: Northwestern University, Evanston, IL (US)

(72) Inventors: Dengke Shen, Evanston, IL (US); James Fraser Stoddart, Evanston, IL (US)

(73) Assignee: Northwestern University, Evanston, IL (US)

( * ) Notice: Subject to any disclaimer, the term of this patent is extended or adjusted under 35 U.S.C. 154(b) by 258 days.

(21) Appl. No.: 17/444,510

(22) Filed: Aug. 5, 2021

(65) Prior Publication Data

US 2022/0040081 A1 Feb. 10, 2022

Related U.S. Application Data

(60) Provisional application No. 63/061,329, filed on Aug. 5, 2020.

(51) Int. Cl.
*A61Q 19/02* (2006.01)
*A61K 8/19* (2006.01)
*A61K 8/365* (2006.01)
*A61K 8/73* (2006.01)

(52) U.S. Cl.
CPC ............... *A61K 8/738* (2013.01); *A61K 8/19* (2013.01); *A61K 8/365* (2013.01); *A61Q 19/02* (2013.01); *A61K 2800/58* (2013.01)

(58) Field of Classification Search
CPC .......... A61K 47/40; A61K 31/60; A61K 8/02; A61K 31/724; A61K 47/6951; A61K 2800/58; A61K 31/5377; A61K 31/4188; A61K 31/506; A61K 8/738; C07D 401/14; C07D 413/14
See application file for complete search history.

(56) References Cited

U.S. PATENT DOCUMENTS

2013/0315848 A1* 11/2013 Beck .................. A61K 8/29 424/59
2017/0137744 A1* 5/2017 Limketkai .............. A61Q 13/00

OTHER PUBLICATIONS

Puchonova et al. Dimeric and different polymeric copper(II) salicylates—Crystal structure and spectral properties. Feb. 24, 2017. Journal of Molecular Structure. vol. 1137. pp. 706-713/ (Year: 2017).*
Zhang, Y. B.; Yang, L. F.; Wang, L. Y.; Duttwyler, S.; Xing, H. B., A Microporous Metal-Organic Framework Supramolecularly Assembled from a Cu-II Dodecaborate Cluster Complex for Selective Gas Separation. Angew. Chem., Int. Ed., 2019, 58, 8145-8150.
Zhang, Y. Y.; Zhang, X.; Lyu, J. F.; Otake, K.; Wang, X. J.; Redfern, L. R.; Malliakas, C. D.; Li, Z. Y.; Islamoglu, T.; Wang, B.; Farha, O. K., A Flexible Metal-Organic Framework with 4-Connected Zr-6 Nodes. J. Am. Chem. Soc., 2018, 140, 11179-11183.
Zhou, H. C.; Long, J. R.; Yaghi, O. M., Introduction to Metal-Organic Frameworks. Chem. Rev., 2012, 112, 673-674.
Zhu, L.; Liu, X. Q.; Jiang, H. L.; Sun, L. B., Metal-Organic Frameworks for Heterogeneous Basic Catalysis. Chem. Rev., 2017, 117, 8129-8176.
Shen, D. K.; Cooper, J. A.; Li, P.; Guo, Q. H.; Cai, K.; Wang X. J.; Wu, H.; Chen, H. L.; Zhang, L.; Jiao, Y.; Qiu, Y. Y.; Stern, C. L.; Liu, Z. C.; Sue, A. C.-H.; Yang, Y.-W.; Alsubaie, F. M.; Farha, O. K.; Stoddart, J. F., Organic Counteranion Co-assembly Strategy for the Formation of Gamma-Cyclodextrin-Containing Hybrid Frameworks. J. Am. Chem. Soc., 2020, 142, 2042-2050.
Adil, K.; Belmabkhout, Y.; Pillai, R. S.; Cadiau, A.; Bhatt, P. M.; Assen, A. H.; Maurin, G.; Eddaoudi, M., Gas/Vapour Separation Using Ultra-Microporous Metal-Organic Frameworks: Insights into The Structure/Separation Relationship. Chem. Soc. Rev., 2017, 46, 3402-3430.
Banerjee, D.; Simon, C. M.; Elsaidi, S. K.; Haranczyk, M.; Thallapally, P. K., Xenon Gas Separation and Storage Using Metal-Organic Frameworks. Chem, 2018, 4, 466-494.
Bao, Z. B.; Xie, D. Y.; Chang, G. G.; Wu, H.; Li, L. Y.; Zhou, W.; Wang, H. L.; Zhang, Z. G.; Xing, H. B.; Yang, Q. W.; Zaworotko, M. J.; Ren, Q. L.; Chen, B. L., Fine Tuning and Specific Binding Sites with a Porous Hydrogen-Bonded Metal-Complex Framework for Gas Selective Separations. J. Am. Chem. Soc., 2018, 140, 4596-4603.
Bennett, T. D.; Cheetham, A. K., Amorphous Metal-Organic Frameworks. Acc. Chem. Res., 2014, 47, 1555-1562.
Carrington, E. J.; McAnally, C. A.; Fletcher, A. J.; Thompson, S. P.; Warren, M.; Brammer, L., Solvent-Switchable Continuous-Breathing Behaviour in a Diamondoid Metal-Organic Framework and Its Influence On CO2 Versus CH4 Selectivity. Nat. Chem., 2017, 9, 882-889.
Chen, K. J.; Scott, H. S.; Madden, D. G.; Pham, T.; Kumar, A.; Bajpai, A.; Lusi, M.; Forrest, K. A.; Space, B.; Perry, J. J.; Zaworotko, M. J., Benchmark C2H2/CO2 and CO2/C2H2 Separation by Two Closely Related Hybrid Ultramicroporous Materials. Chem, 2016, 1, 753-765.
Chen, K. J.; Yang, Q. Y.; Sen, S.; Madden, D. G.; Kumar, A.; Pham, T.; Forrest, K. A.; Hosono, N.; Space, B.; Kitagawa, S.; Zaworotko, M. J., Efficient CO2 Removal for Ultra Pure CO Production by Two Hybrid Ultramicroporous Materials. Angew. Chem., Int. Ed., 2018, 57, 3332-3336.
Chen, T.; Yang, W. H.; Wang, D.; Wan, L. J., Globally Homochiral Assembly of Two-Dimensional Molecular Networks Triggered by Co-Absorbers. Nat. Commun., 2013, 4, 1389.
Chen, Y. F.; Yu, B.; Cui, Y. D.; Xu, S. J.; Gong, J. B., Core-Shell Structured Cyclodextrin Metal-Organic Frameworks with Hierarchical Dye Encapsulation for Tunable Light Emission. Chem. Mater., 2019, 31, 1289-1295.

(Continued)

*Primary Examiner* — Tracy Liu
(74) *Attorney, Agent, or Firm* — Quarles & Brady LLP

(57) ABSTRACT

An organic counteranion co-assembly strategy is employed to prepare a hybrid molecular framework. The hybrid molecular framework comprises an ordered arrangement of cyclodextrin (CD), metal cations, and organic anions.

20 Claims, 18 Drawing Sheets

(56) References Cited

OTHER PUBLICATIONS

Cui, X. L.; Chen, K. J.; Xing, H. B.; Yang, Q. W.; Krishna, R.; Bao, Z. B.; Wu, H.; Zhou, W.; Dong, X. L.; Han, Y.; Li, B.; Ren, Q. L.; Zaworotko, M. J.; Chen, B. L., Pore Chemistry and Size Control in Hybrid Porous Materials for Acetylene Capture from Ethylene. Science, 2016, 353, 141-144.
Della Rocca, J.; Liu, D. M.; Lin, W. B., Nanoscale Metal-Organic Frameworks for Biomedical Imaging and Drug Delivery. Acc. Chem. Res., 2011, 44, 957-968.
Deng, H. X.; Grunder, S.; Cordova, K. E.; Valente, C.; Furukawa, H.; Hmadeh, M.; Gandara, F.; Whalley, A. C.; Liu, Z.; Asahina, S.; Kazumori, H.; O'Keeffe, M.; Terasaki, O.; Stoddart, J. F.; Yaghi, O. M., Large-Pore Apertures in a Series of Metal-Organic Frameworks. Science, 2012, 336, 1018-1023.
Dolomanov, O. V.; Bourhis, L. J.; Gildea, R. J.; Howard, J. A. K.; Puschmann, H., OLEX2: A Complete Structure Solution, Refinement and Analysis Program. J. Appl. Cryst., 2009, 42, 339-341.
Feng, L.; Yuan, S.; Qin, J.-S.; Wang, Y.; Kirchon, A.; Qiu, D.; Cheng, L.; Madrahimov, S. T.; Zhou, H.-C., Lattice Expansion and Contraction in Metal-Organic Frameworks by Sequential Linker Reinstallation. Matter, 2019, 1, 156-167.
Forgan, R. S.; Smaldone, R. A.; Gassensmith, J. J.; Furukawa, H.; Cordes, D. B.; Li, Q. W.; Wilmer, C. E.; Botros, Y. Y.; Snurr, R. Q.; Slawin, A. M. Z.; Stoddart, J. F., Nanoporous Carbohydrate Metal-Organic Frameworks. J. Am. Chem. Soc., 2012, 134, 406-417.
Furukawa, H.; Cordova, K. E.; O'Keeffe, M.; Yaghi, O. M., The Chemistry and Applications of Metal-Organic Frameworks. Science, 2013, 341, 1230444.
Guo, X. X.; Geng, S. B.; Zhuo, M. J.; Chen, Y.; Zaworotko, M. J.; Cheng, P.; Zhang, Z. J., The Utility of the Template Effect in Metal-Organic Frameworks. Coord. Chem. Rev., 2019, 391, 44-68.
Han, S. B.; Wei, Y. H.; Grzybowski, B. A., A Metal-Organic Framework Stabilizes an Occluded Photocatalyst. Chem. Eur. J., 2013, 19, 11194-11198.
Hartlieb, K. J.; Ferris, D. P.; Holcroft, J. M.; Kandela, I.; Stern, C. L.; Nassar, M. S.; Botros, Y. Y.; Stoddart, J. F., Encapsulation of Ibuprofen in CD-MOF and Related Bioavailability Studies. Mol. Pharmaceut., 2017, 14, 1831-1839.
He, H. C.; Hashemi, L.; Hu, M. L.; Morsali, A., The Role of the Counter-Ion in Metal-Organic Frameworks' Chemistry and Applications. Coord. Chem. Rev., 2018, 376, 319-347.
Horike, S.; Shimomura, S.; Kitagawa, S., Soft Porous Crystals. Nat. Chem., 2009, 1, 695-704.
Huang, Z.; White, P. S.; Brookhart, M., Ligand Exchanges and Selective Catalytic Hydrogenation in Molecular Single Crystals. Nature, 2010, 465, 598-601.
Jin, J.; Zhao, X.; Feng, P. Y.; Bu, X. H., A Cooperative Pillar-Template Strategy as a Generalized Synthetic Method for Flexible Homochiral Porous Frameworks. Angew. Chem., Int. Ed., 2018, 57, 3737-3741.
Karmakar, A.; Desai, A. V.; Ghosh, S. K., Ionic Metal-Organic Frameworks (Imofs): Design Principles and Applications. Coord. Chem. Rev., 2016, 307, 313-341.
Katsoulidis, A. P.; Antypov, D.; Whitehead, G. F. S.; Carrington, E. J.; Adams, D. J.; Berry, N. G.; Darling, G. R.; Dyer, M. S.; Rosseinsky, M. J., Chemical Control of Structure and Guest Uptake by a Conformationally Mobile Porous Material. Nature, 2019, 565, 213-217.
Li, P.; Chen, Q.; Wang, T. C.; Vermeulen, N. A.; Mehdi, B. L.; Dohnalkova, A.; Browning, N. D.; Shen, D.; Anderson, R.; Gomez-Gualdron, D. A.; Cetin, F. M.; Jagiello, J.; Asiri, A. M.; Stoddart, J. F.; Farha, O. K., Hierarchically Engineered Mesoporous Metal-Organic Frameworks Toward Cell-Free Immobilized Enzyme Systems. Chem, 2018, 4, 1022-1034.
Li, X.; Guo, T.; Lachmanski, L.; Manoli, F.; Menendez-Miranda, M.; Manet, I.; Guo, Z.; Wu, L.; Zhang, J. W.; Gref, R., Cyclodextrin-Based Metal-Organic Frameworks Particles as Efficient Carriers for Lansoprazole: Study of Morphology and Chemical Composition of Individual Particles. Int. J. Pharm., 2017, 531, 424-432.
Lian, X. Z.; Fang, Y.; Joseph, E.; Wang, Q.; Li, J. L.; Banerjee, S.; Lollar, C.; Wang, X.; Zhou, H. C., Enzyme-MOF (Metal-Organic Framework) Composites. Chem. Soc. Rev., 2017, 46, 3386-3401.
Liu, M.; Zhang, L.; Little, M. A.; Kapil, V.; Ceriotti, M.; Yang, S.; Ding, L.; Holden, D. L.; Balderas-Xicohténcatl, R.; He, D., Barely Porous Organic Cages for Hydrogen Isotope Separation. Science, 2019, 366, 613-620.
Maji, T. K.; Matsuda, R.; Kitagawa, S., A Flexible Interpenetrating Coordination Framework with a Bimodal Porous Functionality. Nat. Mater., 2007, 6, 142-148.
Mason, J. A.; Oktawiec, J.; Taylor, M. K.; Hudson, M. R.; Rodriguez, J.; Bachman, J. E.; Gonzalez, M. I.; Cervellino, A.; Guagliardi, A.; Brown, C. M.; Llewellyn, P. L.; Masciocchi, N.; Long, J. R., Methane Storage in Flexible Metal-Organic Frameworks with Intrinsic Thermal Management. Nature, 2015, 527, 357-361.
Mattia, E.; Otto, S., Supramolecular Systems Chemistry. Nat. Nanotechnol., 2015, 10, 111-119.
Mohamed, M. H.; Elsaidi, S. K.; Pham, T.; Forrest, K. A.; Schaef, H. T.; Hogan, A.; Wojtas, L.; Xu, W. Q.; Space, B.; Zaworotko, M. J.; Thallapally, P. K., Hybrid Ultra-Microporous Materials for Selective Xenon Adsorption and Separation. Angew. Chem., Int. Ed., 2016, 55, 8285-8289.
Morris, R. E.; Brammer, L., Coordination Change, Lability and Hemilability in Metal-Organic Frameworks. Chem. Soc. Rev., 2017, 46, 5444-5462.
Morris, R. E.; Bu, X. H., Induction of Chiral Porous Solids Containing Only Achiral Building Blocks. Nat. Chem., 2010, 2, 353-361.
Patel, H. A.; Islamoglu, T.; Liu, Z. C.; Nalluri, S. K. M.; Samanta, A.; Anamimoghadam, O.; Malliakas, C. D.; Farha, O. K.; Stoddart, J. F., Noninvasive Substitution of K+ Sites in Cyclodextrin Metal-Organic Frameworks by Li+ Ions. J. Am. Chem. Soc., 2017, 139, 11020-11023.
Sakaida, S.; Otsubo, K.; Sakata, O.; Song, C.; Fujiwara, A.; Takata, M.; Kitagawa, H., Crystalline Coordination Framework Endowed with Dynamic Gate-Opening Behaviour by Being Downsized to a Thin Film. Nat. Chem., 2016, 8, 377-383.
Schoedel, A.; Li, M.; Li, D.; O'Keeffe, M.; Yaghi, O. M., Structures of Metal-Organic Frameworks with Rod Secondary Building Units. Chem. Rev., 2016, 116, 12466-12535.
Scott, H. S.; Ogiwara, N.; Chen, K. J.; Madden, D. G.; Pham, T.; Forrest, K.; Space, B.; Horike, S.; Perry, J. J.; Kitagawa, S.; Zaworotko, M. J., Crystal Engineering of a Family of Hybrid Ultramicroporous Materials Based upon Interpenetration and Dichromate Linkers. Chem. Sci., 2016, 7, 5470-5476.
Sheldrick, G. M., A Short History of SHELX. Acta Cryst. A, 2008, 64, 112-122.
Sheldrick, G. M., Crystal structure refinement with SHELXL. Acta Crystallogr C, 2015, 71, 3-8.
Shen, D. K.; Wang, G.; Liu, Z. C.; Li, P.; Cai, K.; Cheng, C. Y.; Shi, Y.; Han, J. M.; Kung, C. W.; Gong, X. R.; Guo, Q. H.; Chen, H. L.; Sue, A. C. H.; Botros, Y. Y.; Facchetti, A.; Farha, O. K.; Marks, T. J.; Stoddart, J. F., Epitaxial Growth of γ-Cyclodextrin-Containing Metal-Organic Frameworks Based on a Host-Guest Strategy. J. Am. Chem. Soc., 2018, 140, 11402-11407.
Sindoro, M.; Yanai, N.; Jee, A. Y.; Granick, S., Colloidal-Sized Metal-Organic Frameworks: Synthesis and Applications. Acc. Chem. Res., 2014, 47, 459-469.
Smaldone, R. A.; Forgan, R. S.; Furukawa, H.; Gassensmith, J. J.; Slawin, A. M. Z.; Yaghi, O. M.; Stoddart, J. F., Metal-Organic Frameworks from Edible Natural Products. Angew. Chem., Int. Ed., 2010, 49, 8630-8634.
Wu, M. X.; Yang, Y. W., Metal-Organic Framework (MOF)-Based Drug/Cargo Delivery and Cancer Therapy. Adv. Mater., 2017, 29, 1606134-1606134.
Wu, Y.; Henke, S.; Kieslich, G.; Schwedler, I.; Yang, M. S.; Fraser, D. A. X.; O'Hare, D., Time-Resolved In-Situ X-ray Diffraction Reveals Metal-Dependent Metal-Organic Framework Formation. Angew. Chem., Int. Ed., 2016, 55, 14081-14084.
Yeung, H. H. M.; Wu, Y.; Henke, S.; Cheetham, A. K.; O'Hare, D.; Walton, R. I., InSitu Observation of Successive Crystallizations and

(56) References Cited

OTHER PUBLICATIONS

Metastable Intermediates in the Formation of Metal-Organic Frameworks. Angew. Chem., Int. Ed., 2016, 55, 2012-2016.

Zhang, J. P.; Liao, P. Q.; Zhou, H. L.; Lin, R. B.; Chen, X. M., Single-Crystal X-Ray Diffraction Studies on Structural Transformations of Porous Coordination Polymers. Chem. Soc. Rev., 2014, 43, 5789-5814.

Zhang, J. P.; Zhou, H. L.; Zhou, D. D.; Liao, P. Q.; Chen, X. M., Controlling Flexibility of Metal-Organic Frameworks. Natl. Sci. Rev., 2018, 5, 907-919.

\* cited by examiner

ORGANIC COUNTERANION CO-ASSEMBLY STRATEGY FOR THE FORMATION OF CYCLODEXTRIN-CONTAINING HYBRID FRAMEWORKS

CROSS-REFERENCE TO RELATED APPLICATIONS

This application claims benefit of priority to U.S. Patent Application Ser. No. 63/061,329, filed Aug. 5, 2020, the contents of which is incorporated by reference in its entirety.

FIELD OF THE INVENTION

The disclosed technology is generally directed to organic frameworks. More particularly the technology is directed to cyclodextrin-containing hybrid frameworks.

BACKGROUND OF THE INVENTION

Metal-organic frameworks (MOFs), which are a class of crystalline porous materials[1] that are constructed[2] from metal ions and organic bridging ligands, give rise to[3-4] highly uniform porous structures with large surface areas. The majority of MOFs are constructed[5] using metal coordination bonds only, and possess[6-7] porous structures from the microscale up to the mesoscale. In contrast, the formation of MOFs with ultramicroporous structures[8] remains challenging.[9] An emerging approach[10-15] to the generation of ultramicroporous hybrid frameworks uses a range of intermolecular interactions to incorporate inorganic anions as the secondary building blocks of the MOFs. The introduction of organic anions that contribute to the construction of MOFs, however, is rarea[16-17] on account of the assembly process often being perturbed by intermolecular interactions,[18] which can preclude co-crystallization or result in disordered guests inside the pores. Thus, the development of new strategies for incorporating organic anions into hybrid frameworks remains a challenging goal in materials science, and has significant ramifications for the design of ultramicroporous architectures.

Lability and flexibility are two unique properties[19-21] of some MOFs, which rely[22] on the reversibility and deformability of coordinative bonds. Reversible metal-ligand bond formation, not only plays an important role in the crystallization process,[23-24] but also allows for post-synthetic modifications of frameworks without changing their overall network structures, e.g., by the exchange of either metals[19] or ligands.[25] In many cases, however, these post-synthetic modifications can lead to changes in the solid-state structures of MOFs, which can have difficulty retaining their crystallinity following this process,[26-27] particularly for a single-crystal to single-crystal transformation involving the rearrangement of metal ions. Reversible structural transformations in MOFs can also be achieved by deforming the coordination geometry[19] of the metal ions in response to the presence of guest molecules, including solvents[28-30] and gases.[31] Although non-solvent organic molecules have served[32-33] as guests for MOFs, their ability to induce reversible structural transformations is yet to be investigated. Furthermore, such structural deformations are typically only observed in MOFs constructed[21] from paddle-wheel organic linkers with two or four connections. Thus, in order to investigate reversible structural transformations, MOFs constructed from different linkers with alternative guest molecules are required.

Recently, we reported[34-37] a class of renewable cyclodextrin-containing MOFs (CD-MOFs), which are assembled from chiral γ-cyclodextrin (γ-CD) building blocks and alkali metal ions. These porous materials[38-39] are a class of cationic MOFs, which possess positively charged frameworks, on account of the coordination between neutral organic ligands and alkali metal cations. In order to balance this positive charge, the OH anions reside inside the porous channels of the frameworks,[34] but in close proximity to the metal centers—to which they experience electrostatic attraction. Although numerous guest molecules have been incorporated[40-43] into CD-MOFs by co-crystallization or absorption, in most instances guest molecules are usually not observable by X-ray crystallography in the solid-state structures.[44]

BRIEF SUMMARY OF THE INVENTION

Disclosed herein is an organic counteranion co-assembly strategy is employed to prepare a hybrid molecular framework. The hybrid molecular framework comprises an ordered arrangement of cyclodextrin (CD), metal cations, and organic anions. In some embodiments, the CD is γ-CD, the organic anion is 4-methoxysalicylate (4-MS), and/or the metal cation is $K^+$.

In another aspect of the invention, the hybrid molecular frameworks disclosed herein may be prepared by preparing a solution comprising the CD, the metal cations, and the organic anions and crystalizing the framework. In some embodiments, the framework is crystalized by vapor diffusion of a precipitant into the solution. In some embodiments, the molar ratio of organic anion to CD in solution is at least 8.0:1.0.

Another aspect of the invention includes skin care products comprising any of the hybrid molecular frameworks described herein. In some embodiments, the skin care product further comprises a skin lotion or a skin cream.

Another aspect of the invention includes a method of whitening skin. The method may comprise contacting skin with any of the skin care products described herein.

These and other aspects of the technology will be described in detail below.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1A:
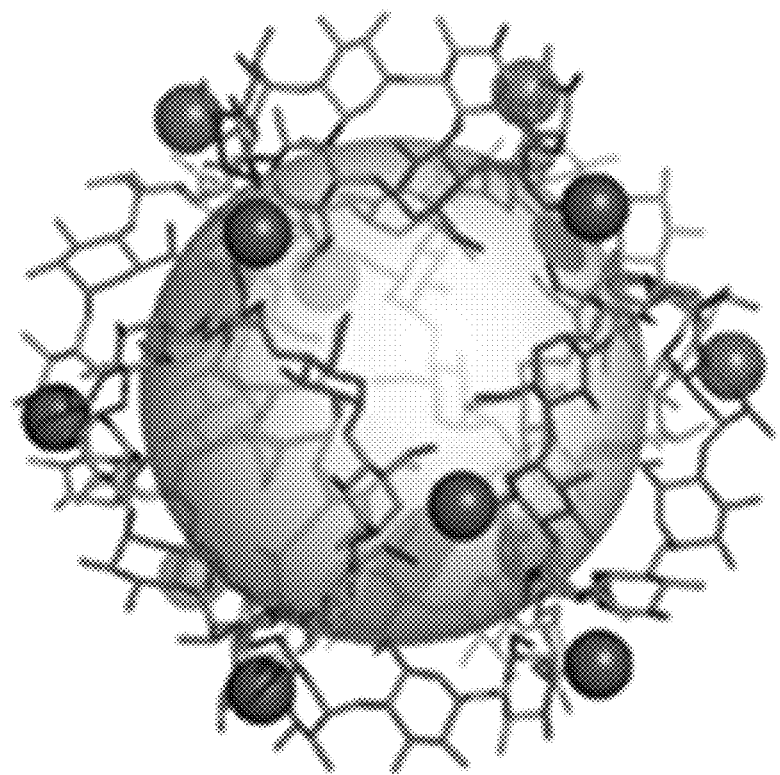
FIG. 1A shows a tubular representation of the solid-state superstructure of the cubic (γ-CD)$_6$ units.

Herein, we report an organic counteranion co-assembly strategy, which introduces organic counterions during the crystallization of cationic MOFs, resulting in hybrid frameworks constructed from a combination of coordinative, electrostatic, and dispersive forces. The resulting crystals exhibit hybrid frameworks that employ CD tori as the primary building blocks coordinated with metal cations that can interact with organic anions. The organic anions act as secondary building blocks, defining the internal porous superstructure of the framework.

As demonstrated in the Examples that follow, a class of cyclodextrin-containing hybrid frameworks (CD-HFs) has been synthesized, employing γ-cyclodextrin (γ-CD) as the primary building blocks, along with 4-methoxysalicylate (4-MS) anions as the secondary building blocks. The CD-HFs are constructed through the synergistic exploitation of coordinative, electrostatic, and dispersive forces. The syntheses have been carried out using an organic counteranion co-assembly strategy, which allows for the introduction of 4-MS$^-$, in place of inorganic OH$^-$, into the cationic γ-CD-containing metal-organic frameworks (CD-MOFs).

Although the packing arrangement of the γ-CD tori in the solid-state superstructure of CD-HFs is identical to that of the previously reported CD-MOFs, CD-HFs crystallize with lower symmetry and in the cuboid space group P43212 when compared to CD-MOF-1, which has the cubic unit cell of I432 space group, on account of the chiral packing of the 4-MS-MS⁻ anions in the CD-HFs superstructures. Importantly, CD-HFs have ultramicroporous apertures associated with the pore channels, a significant deviation from CD-MOF-1 as a consequence of the contribution from the 4-MS-MS⁻ anions, which serve as supramolecular baffles. In gas adsorption-desorption experiments, CD-HF-1 exhibits a Brunauer-Emmett-Teller (BET) surface area of 306 $m^2g^{-1}$ for $CO_2$ at 195 K, yet does not uptake $N_2$ at 77 K, confirming the difference in porosity between CD-HF-1 and CD-MOF-1. Furthermore, the 4-MS⁻ anions in CD-HF-1 can be exchanged with OH anions, leading to an irreversible single-crystal to single-crystal transformation, with rearrangement of coordinated metal ions. Reversible transformations were also observed in CD-MOF-1 when OH⁻ ions were exchanged for 4-MS anions, with the space group changing from I432 to R32. This organic counteranion co-assembly strategy opens up new routes for the construction of hybrid frameworks, which are inaccessible by existing de novo MOF assembly methodologies.

Metal-organic frameworks (MOFs) are a class of hybrid materials comprising inorganic nodes and organic linkers. More specifically, the MOFs have a structure comprising inorganic (e.g., metal) nodes, also referred to as centers, coordinated via organic molecular linkers to form a highly connected porous network. The presently disclosed materials are hybrid molecular frameworks (HFs) as they further comprise organic anions that are present in an ordered arrangement and contribute to the establishment of an ordered superstructure.

The CD-HFs are porous materials constructed from CD-based organic molecular linker coordinated by metal cation nodes. CD is composed of a circular oligomer of five or more α-D-glucopyranosyl residues

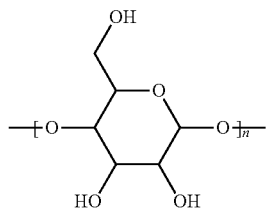

linked 1→4. Suitably, the number of residues n may be greater than or equal to 5 and less than or equal to 15. This includes α-CD, β-CD, and γ-CD, which are 6-, 7-, and 8-membered rings, respectively. The constrained, circular oligomers form tori. The tori have a macrocyclic character that is composed of a central lipophilic cavity and hydrophilic outer surface. The tori also have a truncated cone or "bucket" shape having a primary (1°) Face comprising the C-6 hydroxyl moieties and a secondary (2°) Face comprising the C-2 and C-3 hydroxyl moieties. The CD-HFs built from the CD tori are generally characterized by larger cavities connected be a series of smaller channel-like pores. Charge-balancing counter ions are present in the CD-HF structures to compensate for the metal cation nodes. The charge balancing anions that are initially present in the CD-MOFs are derived from the salts used to synthesize the CD-HFs. For example, if the CD-HFs are crystallized from an organic metal salt, such as potassium 4-methoxysalicylate.

CD-HFs are highly water soluble, non-toxic, and can be constructed from biocompatible CD and biocompatible metals. Additionally, CD-HFs are readily degraded. For example, γ-CD can be hydrolyzed in the presence of α-amylase, whereas α- and β-CD are digestible by intestinal microflora and other microorganisms.

The hybrid molecular frameworks described herein may be used to prepare skin care products. The hybrid molecular frameworks described herein may be incorporated into a skin lotion or cream. Because the hybrid molecular framework displays instability when in contact with water, the organic anions can be released when the compositions are in contact with the moisture on skin. The released organic anions may be used in a number of different skincare applications, including skin whiting. For example, the potassium salt of the organic anion 4-methoxysalicylate is a skin whitening tyrosinase inhibitor and can be used as such when a skin care produce comprising CD-HF is contacted with the skin.

As used herein "cyclodextrin" or "CD" is meant to include circular oligomers of a-D-glucopyranosyl residues and derivatives prepared by the chemical modification of the hydroxyl moieties on either or both of the primary or secondary faces. The chemical modification of the hydroxyl moieties are suitably accomplished prior to assembly of the CD-HF or post-assembly of the CD-HF. Accordingly, the CD-HFs may comprise a CD compound of Formula I

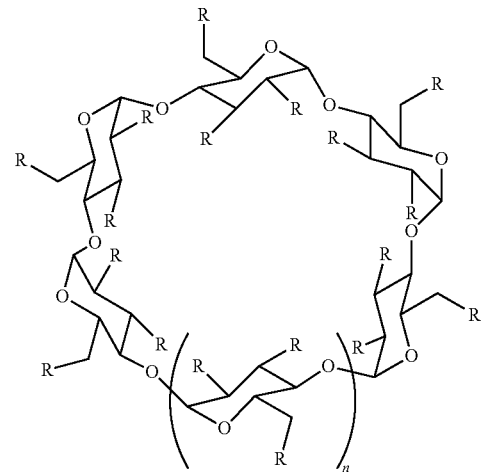

wherein n=0-10; and R is independently selected from the group consisting of —OH; —NR'R"; $C_1$-$C_{18}$ alkyl optionally substituted with one, two, three, four or five $R^1$ groups; $C_2$-$C_{18}$ alkenyl optionally substituted with one, two, three, four or five $R^1$ groups; $C_2$-$C_{18}$ alkynyl optionally substituted with one, two, three, four or five $R^1$ groups; $C_1$-$C_{18}$ alkoxy optionally substituted with one, two, three, four or five $R^1$ groups; —S(=O)$_2$R'; —S(=O)OR'; —S(=O)R'; —C(=O)OR'; —CN; —C(=O)R'; —SR', —N=N⁺=N⁻; —NO$_2$, —OSO$_2$R$^1$; —C(=O)OR', —O(=S)SR', —P(=O)(OR')$_2$; —OP(=O)(OR')$_2$; —P(=O)(OR')R"; —N=R'R"; —NR'P(OR")(OR"); —OC(=O)NR'R"; aryl optionally substituted with one, two, three, four or five $R^2$ groups; heteroaryl optionally substituted with one, two, three, four or five groups independently selected from $R^2$ groups; and cycloalkyl optionally substituted with one, two, three, four or five groups independently selected from $R^2$ groups; wherein each $R^1$ group is independently selected from hydroxyl, halo, lower alkoxy, —NR'R", —S(=O)$_2$R', —S(=O)OR', —S(=O)R', —C(=O)OR', —CN, —C(=O)R', —N=N'=N, —SR', —NO$_2$, —OSO$_2$R', —C(=O)OR', —O(=S)SR', —P(=O)(OR')$_2$, —OP(=O)(OR')$_2$; —P(=O)(OR')R", —N=R'R", —NR'P(OR")(OR'''), —OC(=O)NR'R", aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; wherein each $R_2$ group is independently selected from lower alkyl, lower alkyenyl, lower alkynyl, hydroxyl, halo, lower alkoxy, —NR'R", —S(—O)$_2$R', —S(=O)OR', —S(=O)R', —C(=O)OR', —CN, —C(=O)R', —N=N'=N, —SR', —NO$^2$, —OSO$_2$R$^1$, —C(=O)OR', —O(—S)SR', —P(—O)(OR')$_2$, —OP(=O)(OR')$_2$; —P(=O)(OR')R"; —N=R'R"; —NR'P(OR")(OR'''); —OC(=O)NR'R", aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; and wherein each R' and R" are independently selected from the group consisting of H, lower alkyl and aryl (U.S. Patent Publication No. 2012/0070904).

α-CD, β-CD, and γ-CD in the present invention are meant as a 6-, 7- and 8-membered ring, respectively. In certain embodiments, the R group of α-CD, β-CD, or γ-CD comprises -OH. In other embodiments, the R group of α-CD, β-CD, or γ-CD comprises any of the other groups described above.

"Lower alkyl" in the present invention is meant as a straight or branched chain alkyl radical having, 1-6, and preferably from 1-3, carbon atoms. Examples include but are not limited to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as, for example, a halo, cycloalkyl, aryl, alkenyl or alkoxy group and the like.

"Lower alkenyl" is meant as a straight or branched hydrocarbon radical having from 2 to 6 atoms and one or two double bonds and includes, for example, ethenyl, propenyl, 1-but-3-enyl, 1-pent-3-enyl, 1-hex-5-enyl. The alkenyl group can also be optionally mono-, di-, or trisubstituted with, for example, halo, aryl, cycloalkyl or alkoxy and the like.

"Lower alkynyl" is meant as a straight or branched hydrocarbon radical having from 2 to 6 atoms and one or two triple bonds and includes, for example, propynyl, 1-but-3-ynyl and the like. The alkynyl group can also be optionally mono-, di-, or trisubstituted with, for example, halo, aryl, cycloalkyl or alkoxy and the like.

"Lower alkoxy" is meant as an —O— lower alkyl group wherein lower alkyl is as defined above.

"Halo" or "halogen" is meant as a halogen radical of fluorine, chlorine, bromine or iodine.

"Aryl" is meant as an aromatic carbocylic radical having a single ring (e.g. phenyl), multiple rings (e.g. biphenyl) or multiple fused rings in which at least one is aromatic (e.g. 1,2,3,4-tetrahydronaphthyl).

"Heteroaryl" is meant as one or multiple fused aromatic ring systems of 5-, 6- or 7-membered rings containing at least one and up to four heteroatoms selected from nitrogen, oxygen or sulfur. Examples include but are not limited to furanyl, thienyl, pyridinyl, pyrimidinyl, benzimidazolyl and benzoxazolyl.

"Cycloalkyl" is meant as a carbocylic radical having a single ring (e.g. cyclohexyl), multiple rings (e.g. bicyclohexyl) or multiple fused rings (e.g.). In addition, the cycloalkyl group may have one or more double bonds.

CD-HFs comprise an organic metal salt component. The organic metal salt component comprises coordinating metal cations. The coordinating metal cations act as nodes or centers to coordinate the organic CD linkers to form highly connected porous networks. The metal cations may be suitably selected from metal cations capable of forming complexes with carbohydrates. The metal cations may be independently selected from 1+, 2+, or 3+ cations. The metal cations may be independently selected from Group I (Alkali) metal cations, Group II (Alkaline earth) metal cations, transition metal cations, lanthanoid metal cations, or post-transitional metal cations. Examples of metal cations include, without limitation, $Li^+$, $Na^+$, $K^+$, $Rb^+$, $Cs^+$, $Mg^{2+}$, $Ca^{2+}$, $Sr^{2+}$, $Ba^{2+}$, $Ag^+$, $Cd^{2+}$, $La^{3+}$, $Yb^+$, $Sn^{2+}$, $Pb^{2+}$. In some embodiments, the metal cations are selected from Group I transition metals, suitably $Li^+$, $Na^+$, $K^+$, $Rb^+$, or $Cs^+$.

The organic metal salt also comprises an organic anion. The organic anion contributes the overall superstructure by modulating the interaction between the CD and metal cations, interacting with other organic anions, and interacting directly with the CD and metal cation. As a result of these various interactions, the organic anion are secondary building blocks leading to the generation of new porous materials. Organic anions suitable for use to prepare the CD-HF materials may include carboxylate (—COO$^-$) moieties and the like. Suitably the organic anion comprises an aromatic moiety that may allow for [π . . . π] stacking. An exemplary organic anion for use with the present technology is 4-MS$^-$.

As demonstrated in the Examples, the participation of the organic anions allows for the preparation of ultramicroporous materials that may selectively adsorb gases. Adsorption experiments show that the present materials may selectively adsorb $CO_2$ while exhibiting little to no adsorption of $N_2$.

Crystalline compositions may be prepared from CD-HFs described herein. The crystalline composition may have a packing arrangement categorized by a cuboid space group. Exemplary crystalline packing arrangements and unit cell dimensions are provided in Table 1.

Generally, CD-HFs are prepared by dissolution of both the cyclodextrin component and the organic metal salt component in any solvent in which both have solubility. Isolation of CD-HFs is done by addition of a second solvent in which either of the components has poor solubility, including, but not limited to, $C_1$-$C_{18}$ alcohols, acetone, tetrahydrofuran, dioxane, acetonitrile, as well as other common organic solvents miscible with water, or any mixtures thereof. As such, in a specific non-limiting embodiment of the invention, methanol is allowed to vapor diffuse into an aqueous solution containing the CD and metal organic salt.

The organic metal salt component to be dissolved into solution with the CD may be added in any appropriate molar or equivalent ratio that allows for the formation of the CD-HF. Suitably, the organic metal salt may be provided in a molar ratio to the cyclodextrin component of at least 8.0:1.0. In some embodiments, the organic metal salt may be provided in a molar ratio to the cyclodextrin component of at least 16.0:1.0 or at least 32.0:1.0.

Although the metal cation and organic anion may be added together as an organic metal salt, each of the components may be contributed separately to the solution such as by dissolution of two different salts, a first comprising the metal cation and a second comprising the organic anion. Suitably, each of the metal cation and organic anion, independently, may be provided in a molar ratio to the cyclodextrin component of at least 8.0:1.0. In some embodiments, each of the metal cation and organic anion, independently, may be provided in a molar ratio to the cyclodextrin component of at least 16.0:1.0 or at least 32.0:1.0.

In summary, we have introduced a new organic counteranion co-assembly strategy for the synthesis of hybrid frameworks that exploits interactions between the organic counteranions and the frameworks, in conjunction with the interactions between counteranions and metal cations, as well as counteranions with each other. As demonstrated in the Examples, 4-Methoxysalicylate organic anions were introduced into the assembly with γ-CD tori and $K^+$ ions, and served as secondary building blocks in the construction of the γ-cyclodextrin-containing hybrid frameworks, CD-HFs, by acting as linkers through hydrogen bonding interactions between adjacent γ-CD tori. In comparison with CD-MOF-1, which is composed of only coordinative bonds, CD-HF-1 is constructed from a combination of coordinative, electrostatic, and dispersive forces, and exhibits improved stability compared to that of CD-MOFs. CD-HFs exhibit the same packing of organic ligands as CD-MOFs, but possess different space groups and porosities. Importantly, 4-$MS^-$ anions participate in the construction of the hybrid frameworks and serve as supramolecular baffles, resulting in ultramicroporous apertures associated with the pore channels, allowing the CD-HFs to uptake gas molecules selectively. Furthermore, the hybrid frameworks can undergo an irreversible single-crystal to single-crystal transformation from CD-HFs to CD-MOFs, through the removal of 4-MS-$MS^-$ anions using anion exchange, leading to the rearrangement of the coordinated K cations to different coordinative sites. This transformation indicates that the formation of CD-HFs is a consequence of several interactions acting in concert: (i) the coordination between metal cations and neutral organic ligands, (ii) the intermolecular interactions between the organic counteranions and organic ligands, and (iii) the electrostatic interactions between metal cations and organic counteranions. In addition, anion exchange using OH and 4-MS-$MS^-$ anions enables CD-MOF-1 to undergo reversible deformation between the 1432 and $R^{32}$ space groups, respectively, demonstrating that CD-MOF-1 is structurally flexible with eight-connected organic ligands. Finally, the synthesis of CD-HFs using this new organic counteranion co-assembly strategy, not only represents a significant addition to the family of hybrid frameworks, but also provides fundamental insights into the design of ultramicroporous materials, and offers the potential to develop a wider variety of applications for these green and porous extended framework materials.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Figure 5A:
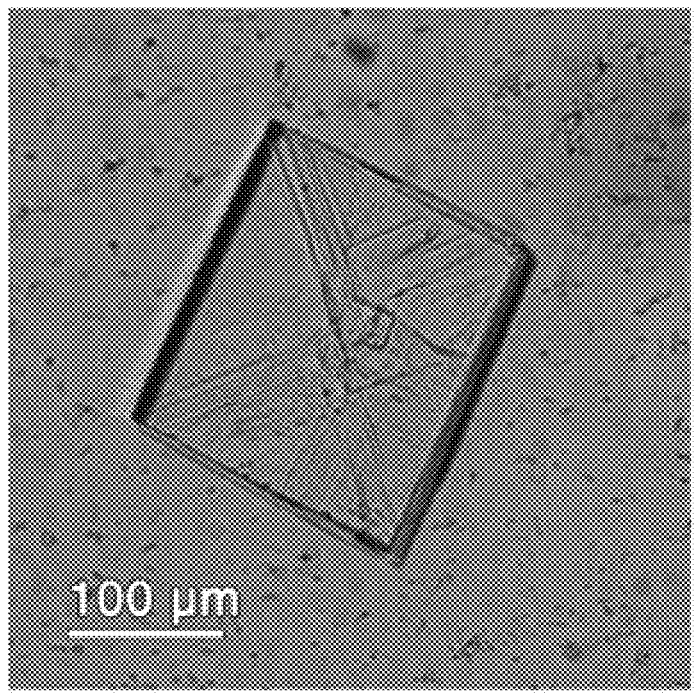
FIG. 5A provides an optical microscope image of CD-HF-1 without a polarizing filter.
Figure 5B:
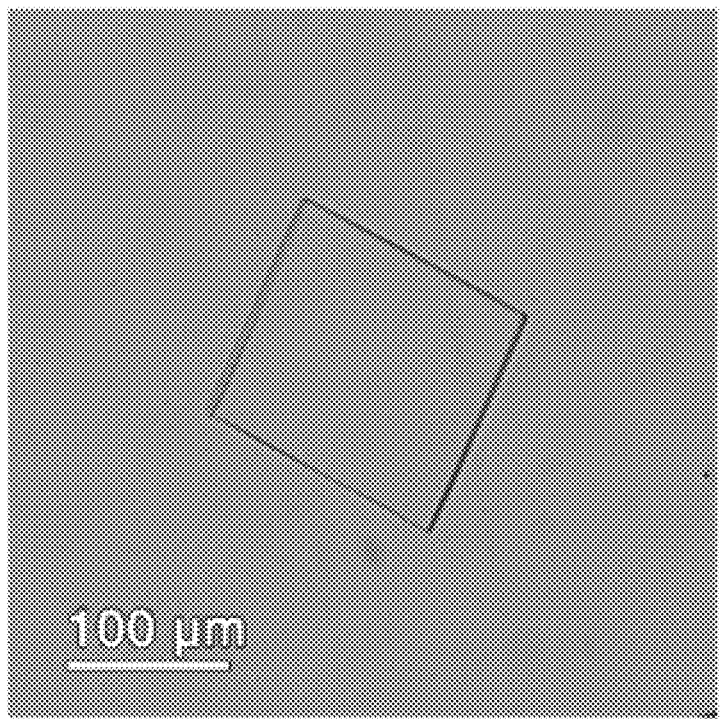
FIG. 5B provides an optical microscope image of CD-MOF-1 without a polarizing filter.

The synthetic protocol for CD-HFs is similar to the procedure[34-35] used to produce CD-MOF-1, but employs 4-MSK instead of potassium hydroxide as the source of potassium ions. MeOH vapor was diffused into an aqueous solution of 0.8 M 4-MSK and 25 μM γ-CD for 7 days, resulting in cubic crystals of CD-HF-1 with visible diagonal lines (FIG. 5A) in approximately 50% yield. After redissolving the crystals in $D_2O$, the number of counteranions in the frameworks was deduced from the 1H NMR spectrum (FIG. 1C), which revealed that 4-$MS^-$ anions were incorporated into the crystal in a ratio of 2:1 with respect to γ-CD tori.[45]

Single-crystal X-ray analysis (Table 1) revealed that CD-HF-1 crystallizes in the cuboid space group P43212 with unit cell dimensions of 31×31×61.3 Å and with enantiomorphic symmetry. These properties deviate from those observed for CD-MOF-1, which crystallizes in the 1432 space group, with unit cell parameters of approximately 31 $Å^3$. Powder X-ray diffraction (PXRD) patterns (FIG. 1D) corroborated these findings, with a significant difference in the peak observed at 5.6° between samples of CD-MOF-1 and CD-HF-1, which confirmed the lower symmetry of CD-HF-1.

Figure 2A:
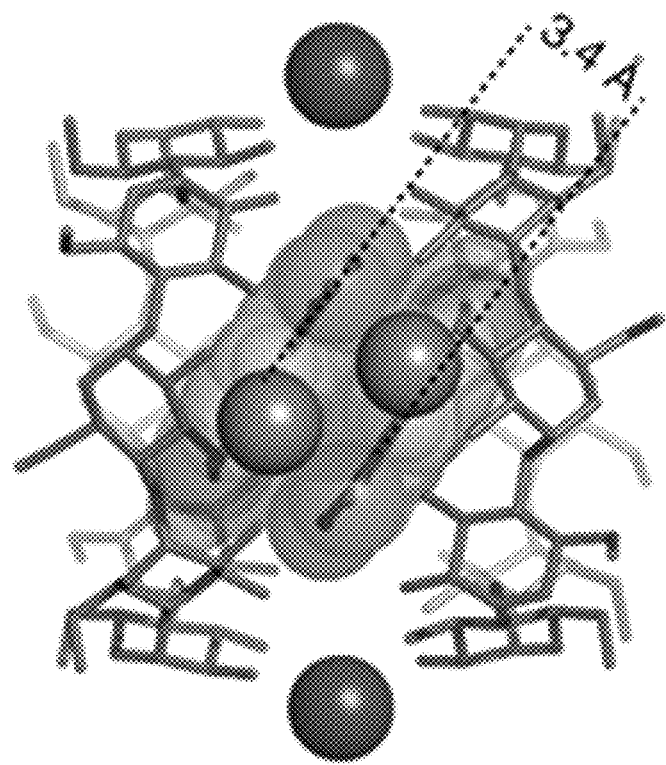
FIG. 2A provides a stick representation of the solid-state superstructure of the γ-CD dimer parallel to c-axis in CD-HF-1, with two 4-MS-MS$^-$ anions represented in space-filling mode, showing a distance of 3.4 Å commensurate with [π . . . π] stacking.
Figure 2B:
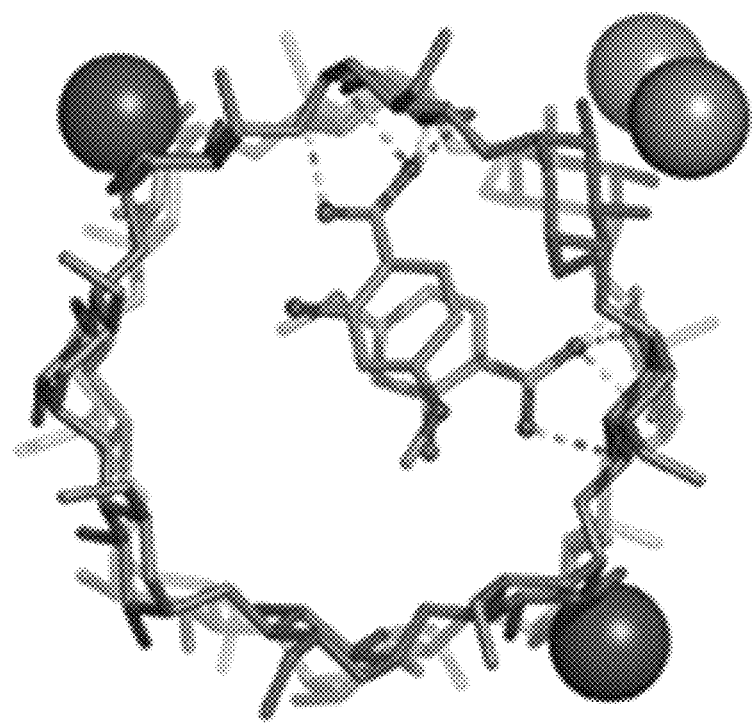
FIG. 2B provides a stick representation of the solid-state superstructure of the γ-CD dimer parallel to c-axis in CD-HF-1, with hydrogen bonds illustrated by dashes, highlighting the contribution of intermolecular forces.
Figure 2C:
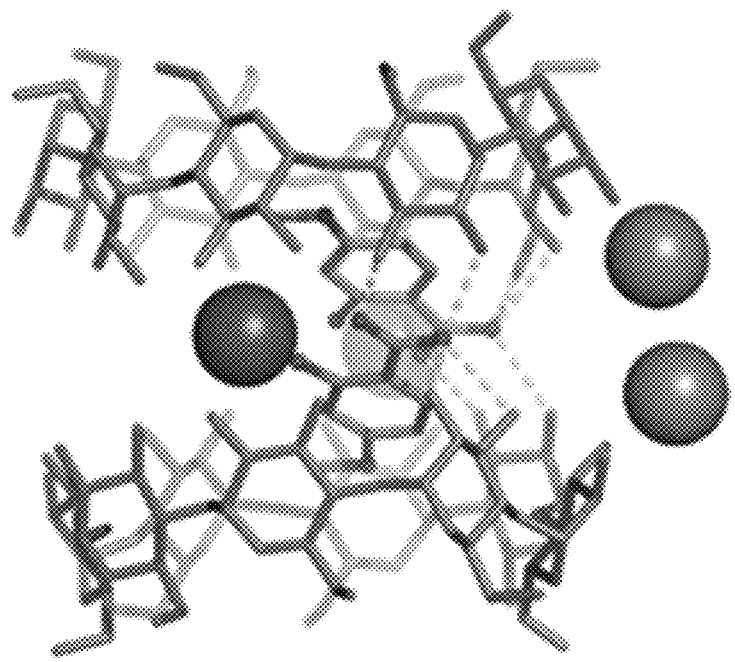
FIG. 2C provides a stick representation of the solid-state superstructure of the γ-CD dimer parallel to c-axis in CD-HF-1, with hydrogen bonds illustrated by dashes, highlighting the contribution of intermolecular forces.
Figure 2D:
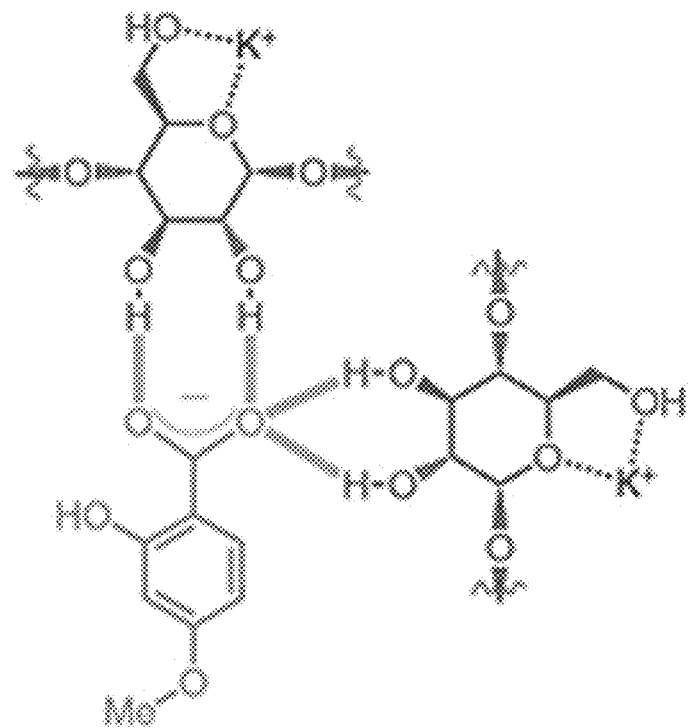
FIG. 2D shows a schematic diagram indicating the nature of the link between the two γ-CD tori of the dimer parallel to the c-axis in CD-HF-1, with the 4-MS$^-$ anion acting as the bridge, forming four hydrogen bonds between the carboxylate moiety of a 4-MS$^-$ anion and two pairs of C-2 and C-3 hydroxyl groups from the secondary faces of γ-CD tori.
Figure 2E:
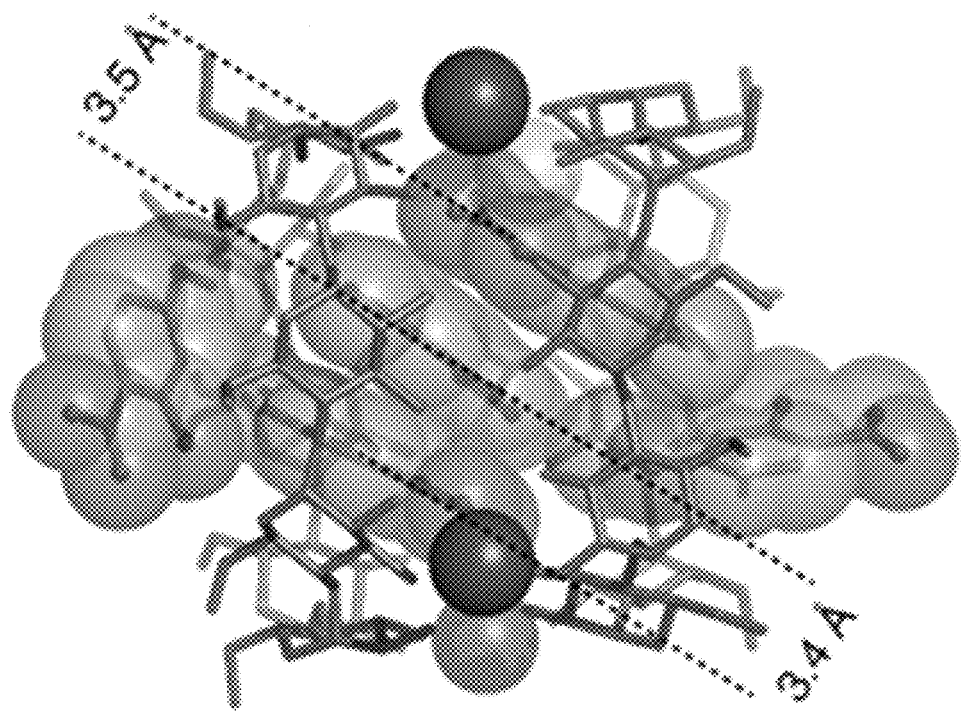
FIG. 2E provides a stick representation of the solid-state superstructure of the γ-CD dimer parallel to the a- or b-axis in CD-HF-1, with five 4-MS$^-$ anions represented in space-filling mode, three of which show distances of 3.5 and 3.4 Å, commensurate with [π . . . π] stacking.
Figure 2F:
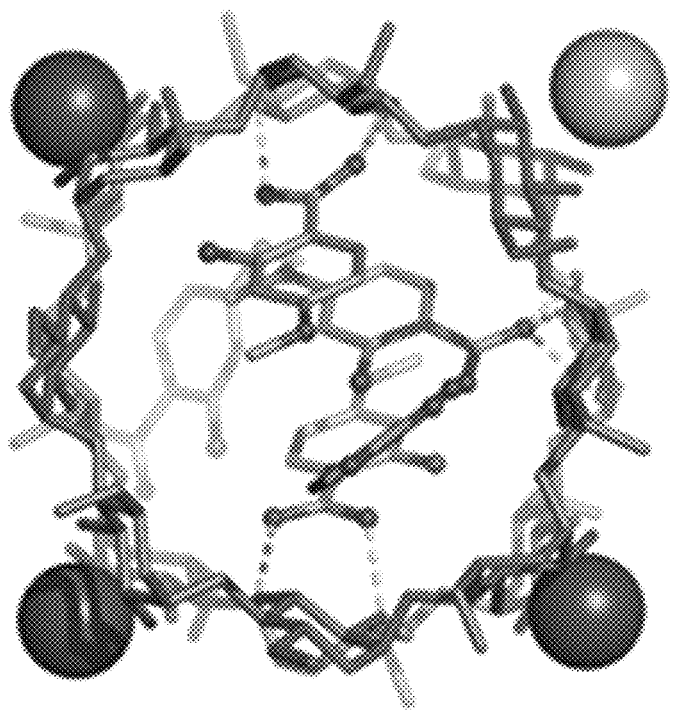
FIG. 2F provides a stick representation of the solid-state superstructure of the γ-CD dimer parallel to the a- or b-axis in CD-HF-1, with hydrogen bonds illustrated as dashes, highlighting the contribution of intermolecular forces.
Figure 2G:
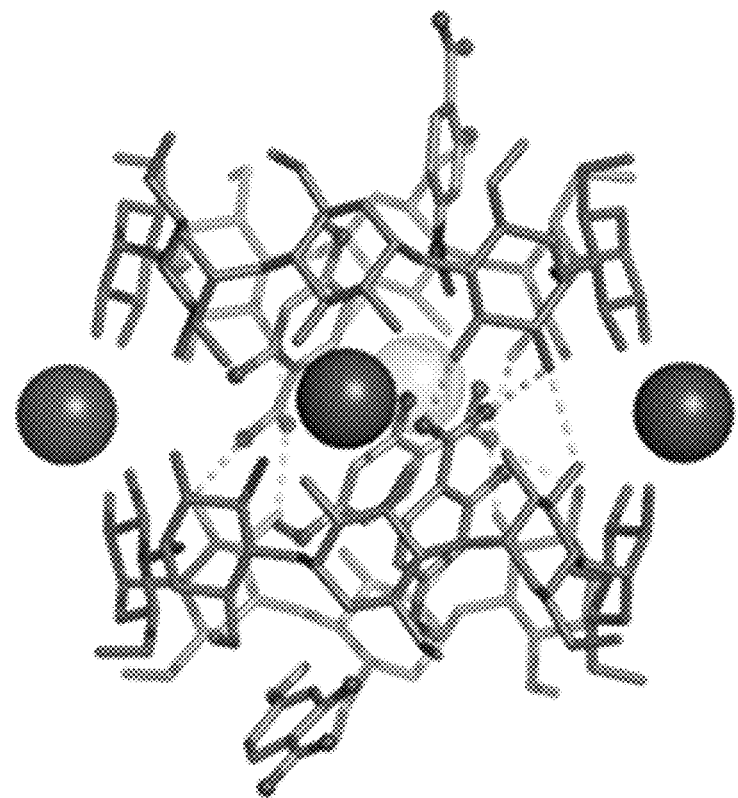
FIG. 2G provides a stick representation of the solid-state superstructure of the γ-CD dimer parallel to the a- or b-axis in CD-HF-1, with hydrogen bonds illustrated as dashes, highlighting the contribution of intermolecular forces.
Figure 2H:
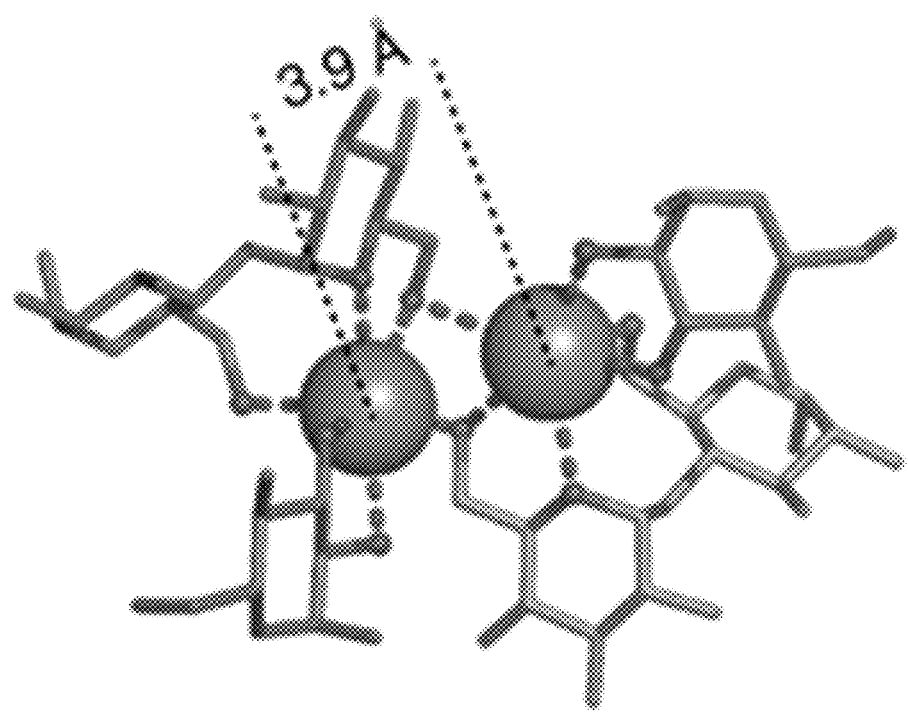
FIG. 2H provides a stick representation of the of K$^+$ ion-pair, each of which has six coordination bonds illustrated as dashes to the primary faces of two γ-CD tori and the secondary face of another γ-CD tori.
Figure 2I:
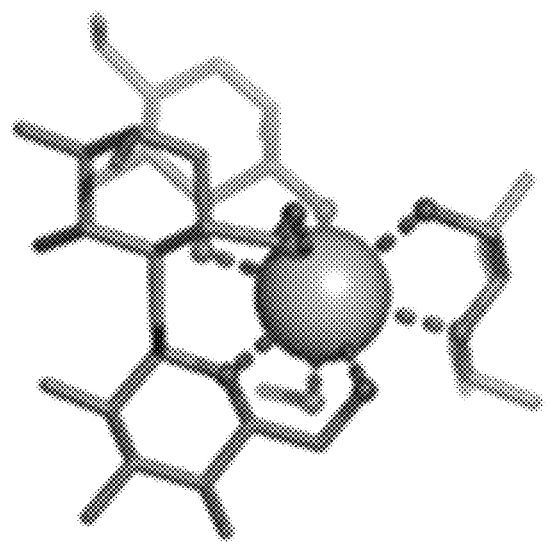
FIG. 2I provides a stick representation of the K$^+$ ion, with eight coordination bonds illustrated as dashes to the primary faces of two γ-CD tori and the secondary face of another γ-CD tori, along with a single MeOH molecule.
Figure 2J:
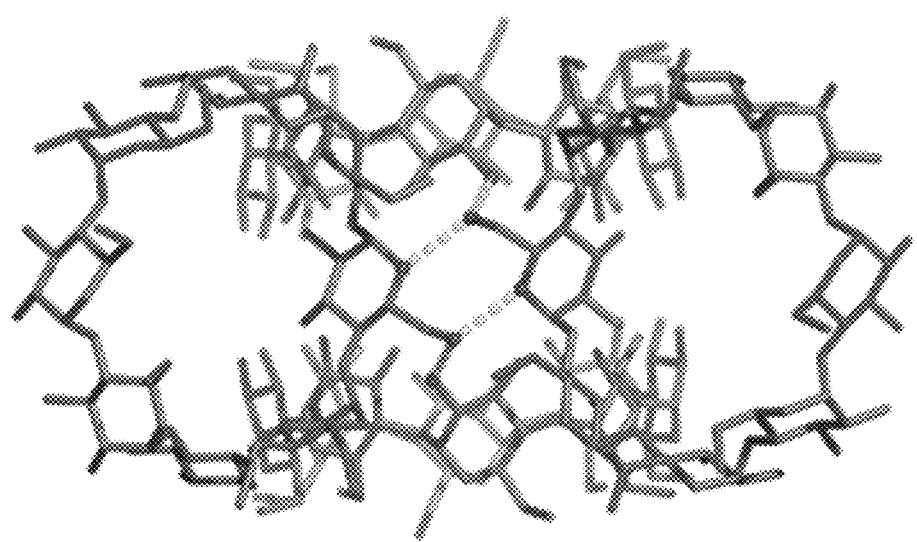
FIG. 2J provides a stick representation of the solid-state superstructure showing the blank coordination position associated with four γ-CD tori—i.e., a K$^+$ cation is absent-located diagonally to the K$^+$ ion-pairs, with the four hydrogen bonds between the γ-CD tori illustrated as dashed lines.

The γ-CD dimers aligned parallel to the a- and b-axes (FIG. 2E-2G) are isostructural, wherein the secondary faces of the γ-CD tori of each dimer coordinate to four $K^+$ ions.

TABLE 1

A Summary of Crystallographic Data For CD-MOFs and CD-HFs

| | Molecular Formula | Crystal System | Space Group | a, b/Å | c/Å | α, β/° | γ/° | $R_1$ | $wR_2$ | Flack Parameter | Yield/% |
|---|---|---|---|---|---|---|---|---|---|---|---|
| CD-MOF-1 | n($C_{48}H_{80}O_{40}$), 2 n(K O H) | Cubic | I 4 3 2 | 31.006 (8) | 31.006 (8) | 90 | 90 | 0.2391 | 0.5723 | 0.3 | 70 |
| CD-HF-1 | 3 n($C_{48}H_{80}O_{40}$), 6 n $K^+$ 5.5 n($C_8H_7O_4$), | Cuboid | P $4_3 2_1 2$ | 31.2120 (12) | 61.302 (3) | 90 | 90 | 0.0736 | 0.2147 | 0.019 | 50 |
| CD-HF-0.9 | 3 n($C_{48}H_{80}O_{40}$), 6 n $K^+$ 5 n($C_8H_7O_4$), | Cuboid | P $4_3 2_1 2$ | 31.089 (2) | 61.485 (6) | 90 | 90 | 0.0732 | 0.2073 | 0.067 | 48 |
| CD-MOF-1 ⊃ (4-MS⁻) 0.85 | $C_{48}H_{80}O_{40}$, 2 n $K^+$ | Cubic | I 4 3 2 | 31.0134 (14) | 31.0134 (14) | 90 | 90 | 0.1085 | 0.3410 | 0.061 | 36 |
| CD-MOF-1-Exchange | $C_{48}H_{80}O_{40}$, 2 n $K^+$ | Cubic | I 4 3 2 | 31.0097 (6) | 31.0097 (6) | 90 | 90 | | | | |
| CD-MOF-1 ⊃ (4-MS⁻) 0.5 | $C_{48}H_{80}O_{40}$, 2 n $K^+$ | Trigonal | R 3 2 | 43.512 (6) | 27.788 (5) | 90 | 120 | 0.0665 | 0.2115 | 0.082 | |

Figure 1B:
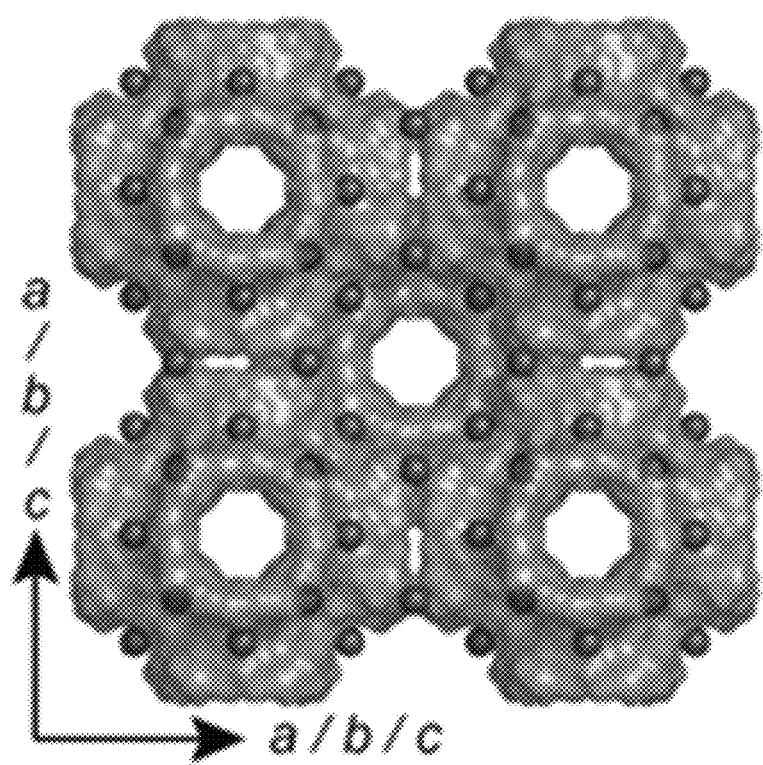
FIG. 1B shows a space-filling representation of the extended body-centered cubic packing of CD-MOF-1, with γ-CD and $K^+$ ions represented in light grey and dark grey respectively.
Figure 1C:
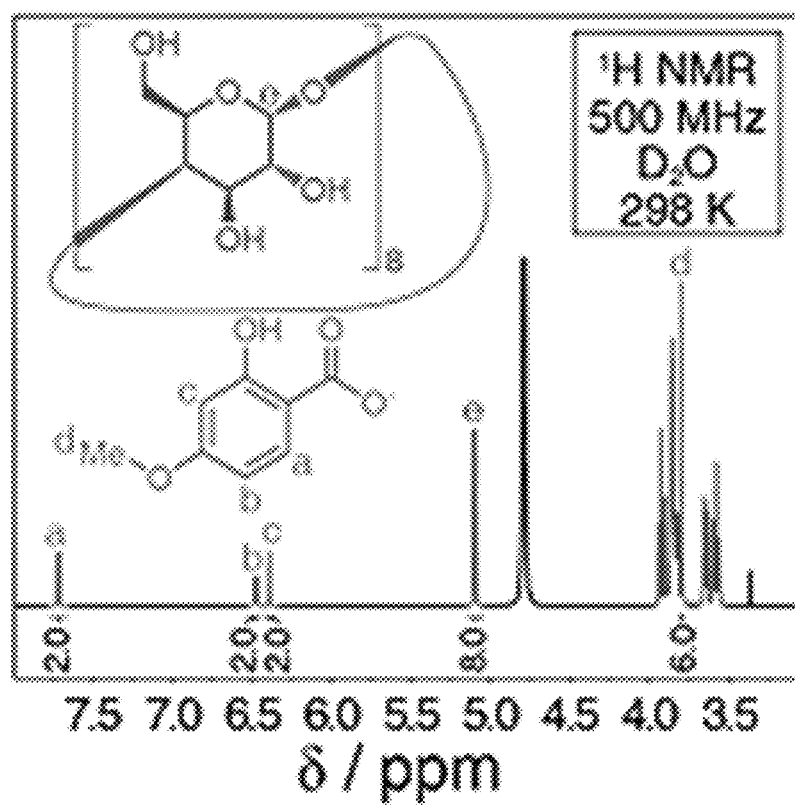
FIG. 1C provides a 1H NMR Spectrum (500 MHZ, D$_2$O, 298 K) of CD-HF-1 with protons of γ-CD and the protons of 4-methoxysalicylate (4-MS$^-$), reveals the presence of a 2:1 ratio of 4-MS$^-$:γ-CD.
Figure 1D:
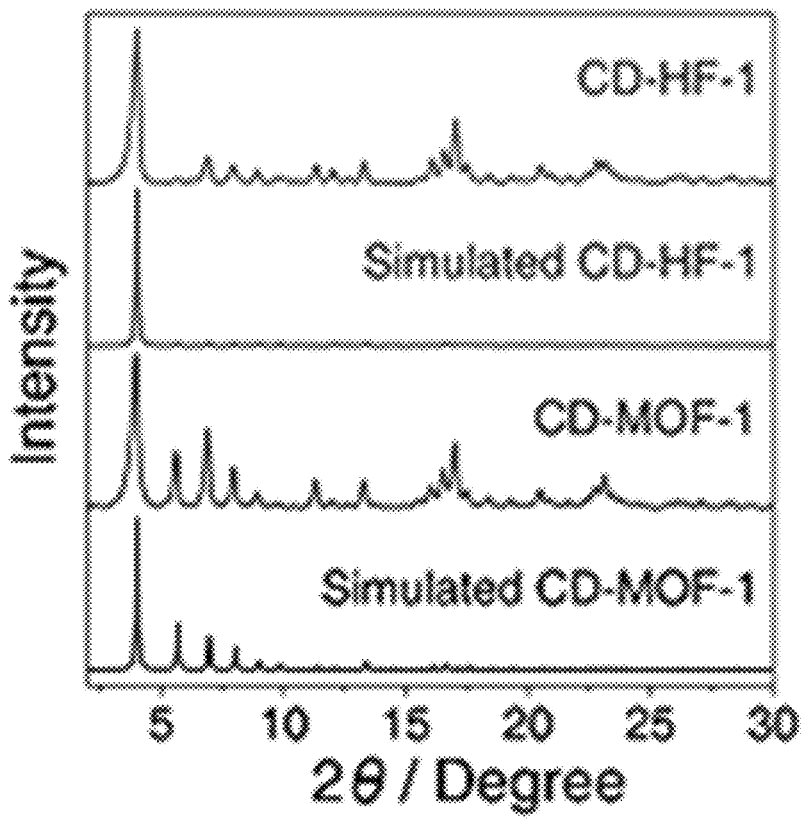
FIG. 1D provides powder X-ray diffraction of CD-MOF-1 and CD-HF-1 compared with the predicted I432 diffraction patterns of CD-MOF-1 and P43212 diffraction patterns of CD-HF-1.
Figure 1E:
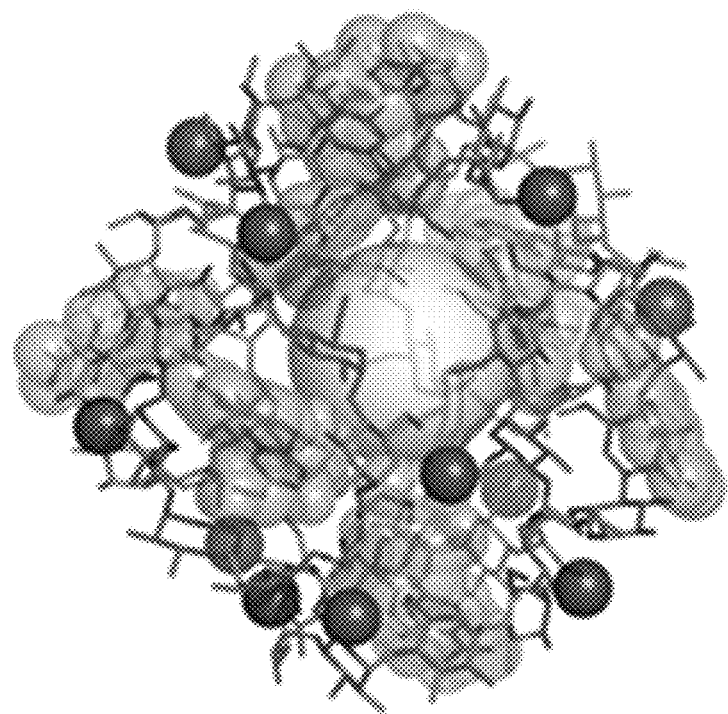
FIG. 1E shows a tubular representation of the solid-state superstructure of the cubic $(\gamma\text{-CD})_6$ units.
Figure 1F:
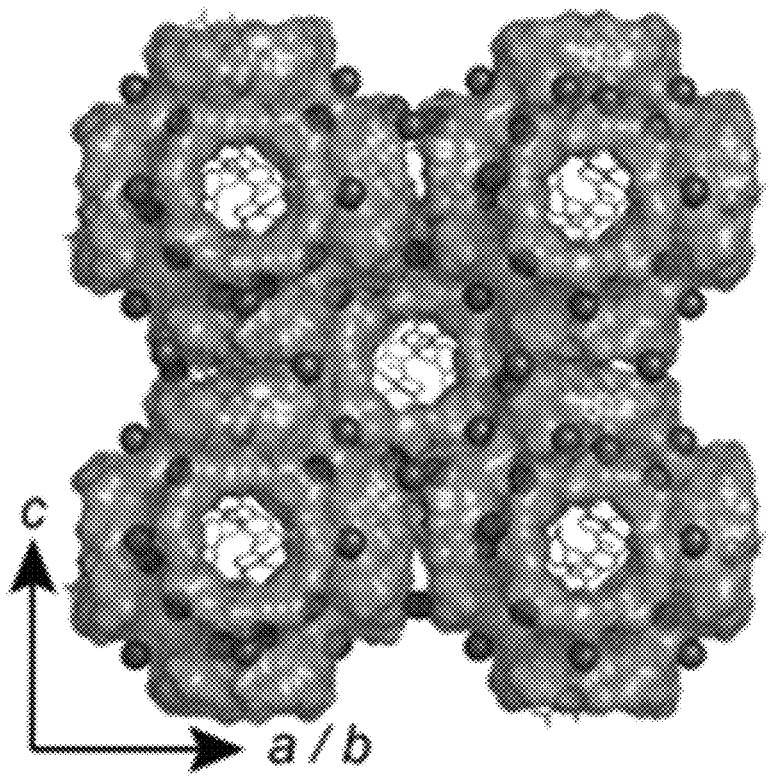
FIG. 1F shows a space-filling representation of the extended body-centered cubic packing viewed from a- or b-axis.
Figure 1G:
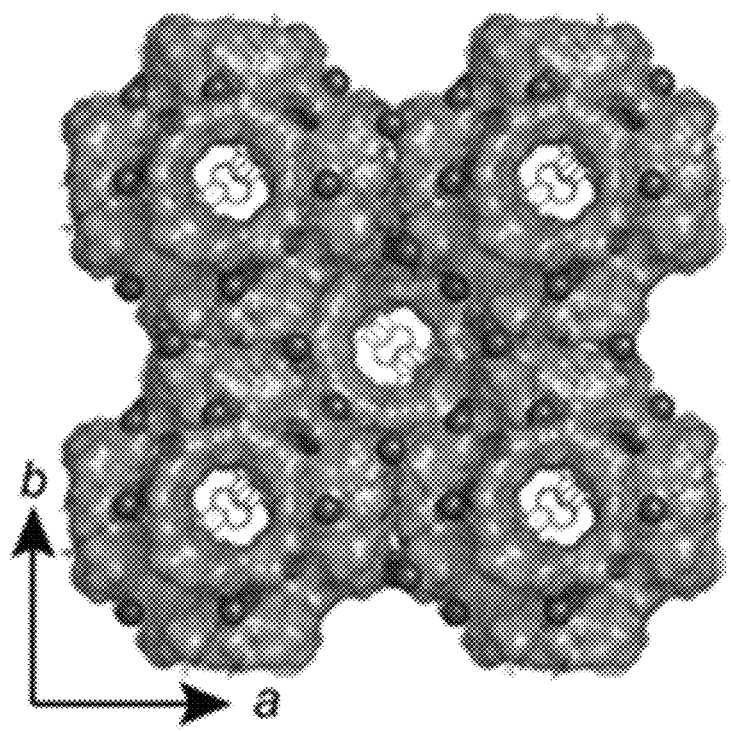
FIG. 1G shows a space-filling representation of the extended body-centered cubic packing viewed from c-axis.

The solid-state superstructure of CD-HF-1 exhibits (FIG. 1E-1G) body-centered cubic packing of the (γ-CD)$_6$ cubic units, which are in the same arrangement as in CD-MOF-1 (FIG. 1A-1B). The (γ-CD)$_6$ cube (FIG. 1A, 1E) is constructed from six γ-CD tori, which comprise the faces of the cube. The crystal superstructure also reveals that the K ions in CD-HF-1 are present in a ratio of 2:1 with respect to γ-CD, confirming that all 4-MS-MS⁻ anions are charge balanced with $K^+$ cations, indicating that none of the γ-CD tori in CD-HF-1 have been deprotonated.[46]

Figure 1H:
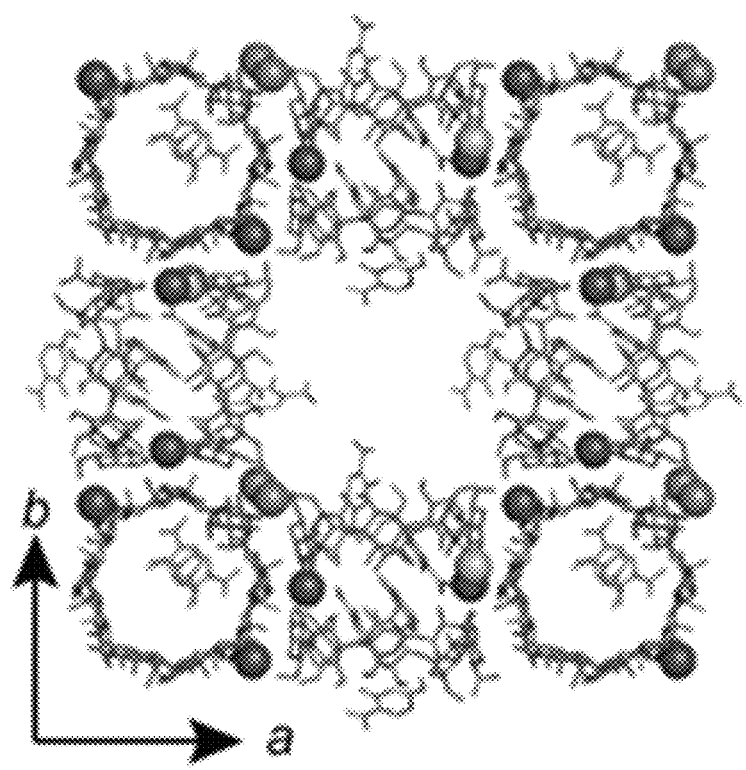
FIG. 1H provides a tubular representation of the slice through CD-HF-1, showing a single layer of γ-CD dimers.

The positions of the 4-MS-MS⁻ anions and K cations in the solid-state superstructure of CD-HF-1 become evident upon viewing along different axes (FIG. 1F-1G), as well as by taking a slice through CD-HF-1, whereupon a layer of "dimers"[47] (FIG. 1H) of γ-CD become visible. FIGS. 2A-2J show the detailed superstructural characteristics of these γ-CD dimers along different axes, and helps to understand the nature of these frameworks. In the case of the γ-CD dimer parallel to the c-axis (FIG. 2A-2C), two of the $K^+$ ions are eight-coordinate while the other two are in close proximity to one another (see $K^+$, FIGS. 2A and 2H), with a limited separation of 3.9 Å. Each of the $K^+$ ion-pairs is six-coordinated by the primary faces of two γ-CD tori and the secondary face of a third γ-CD. Two crystallographically equivalent 4-MS-MS⁻ anions reside inside the cavity of this γ-CD dimer and are ipsilateral to the K ion-pairs, suggesting that the locations of the 4-MS-MS⁻ anions and these $K^+$ ions are dependent on one another. The plane-to-plane distance (FIG. 2A) between the two 4-MS-MS⁻ anions inside the c-axial γ-CD dimer is 3.4 Å, implying the existence of [π ... π] stacking interactions between them. Importantly, each carboxyl group associated with these two 4-MS-MS⁻ anions residing in the middle of the gap between the two γ-CD tori forms (FIG. 2C-2D) four hydrogen bonds to the dimer through short [O ... O] contacts (2.6-2.7 Å), demonstrating that these organic anions stabilize the links between the two γ-CD tori through intermolecular interactions as well as coordinative bonds. The existence of the K ion-pair in the γ-CD dimer also leads (FIG. 2B) to a vacant coordination site, situated diagonally with respect to the K ion-pairs, where, in lieu of coordinating to a metal center, the four γ-CD tori are held together through four hydrogen bonds, as indicated (FIG. 2J) by two pairs of short [O ... O] contacts.[48]

One of these $K^+$ ions is different from those present in CD-MOF-1 (see $K^+$, FIGS. 2F, 2G, and 2I) since it interacts (FIG. 2I) with the primary faces of two γ-CD tori and the secondary face of only one γ-CD, in addition to a MeOH molecule.[49] For every γ-CD dimer that lies parallel to the a- and b-axes, four 4-MS-MS⁻ anions with 100% occupancy and one with 50% occupancy are located in the solid-state superstructure. Three of these 4-MS-MS⁻ anions are located (FIG. 2E) inside the γ-CD dimer, separated by distances of 3.5 and 3.4 Å, wherein all their carboxyl groups are arrayed (FIG. 2G) at the waistline of the dimer. The γ-CD tori exhibit significant deformations, on account of the eight pairs of hydrogen bonds between the carboxyl groups of these 4-MS-MS⁻ anions and the hydroxyl groups of the γ-CD dimer, indicating that the formation of this host-guest complex is stabilized by these noncovalent bonding, as well as coordinative, interactions. Furthermore, short [O ... O] contacts were observed (FIG. 2G) between the neighboring γ-CD tori, with mean distances[50] of 2.8 Å, demonstrating[51] the direct contribution of hydrogen bonds to the connections between the γ-CD building blocks. These three 4-MS-MS⁻ anions occupy most of the cavities in the γ-CD dimers lying parallel to the a- and b-axes, while the remaining one 4-MS-MS⁻ counteranion with 100% occupancy, and another with 50% occupancy, are found to invade (FIG. 1H) the space near the center of the cavity of the (γ-CD)$_6$ cube. Half of the fully occupied 4-MS-MS⁻ anion is located inside the dimer, and the other half, containing the carboxyl group, points into the cavity of the (γ-CD)$_6$ cube. The remaining 4-MS-MS⁻ anion with 50% occupancy resides completely inside the cavity of the (γ-CD)$_6$ cube. Notably, no hydrogen bonds were observed between the γ-CD building blocks and these 4-MS-MS⁻ anions in the cubic cavity, suggesting that they may not contribute to the construction of the frameworks, on account of their positioning most likely being determined by steric constraints and electrostatic attraction to the $K^+$ ions. After evaluating the 1H NMR spectroscopic and the X-ray crystallographic data, we found that 8.3% of the 4-MS-MS⁻ anions are absent in the crystal superstructure, suggesting that the other 50% occupancy of the half-occupied 4-MS-MS⁻ anion is disordered within the crystal superstructure.

Figure 6:
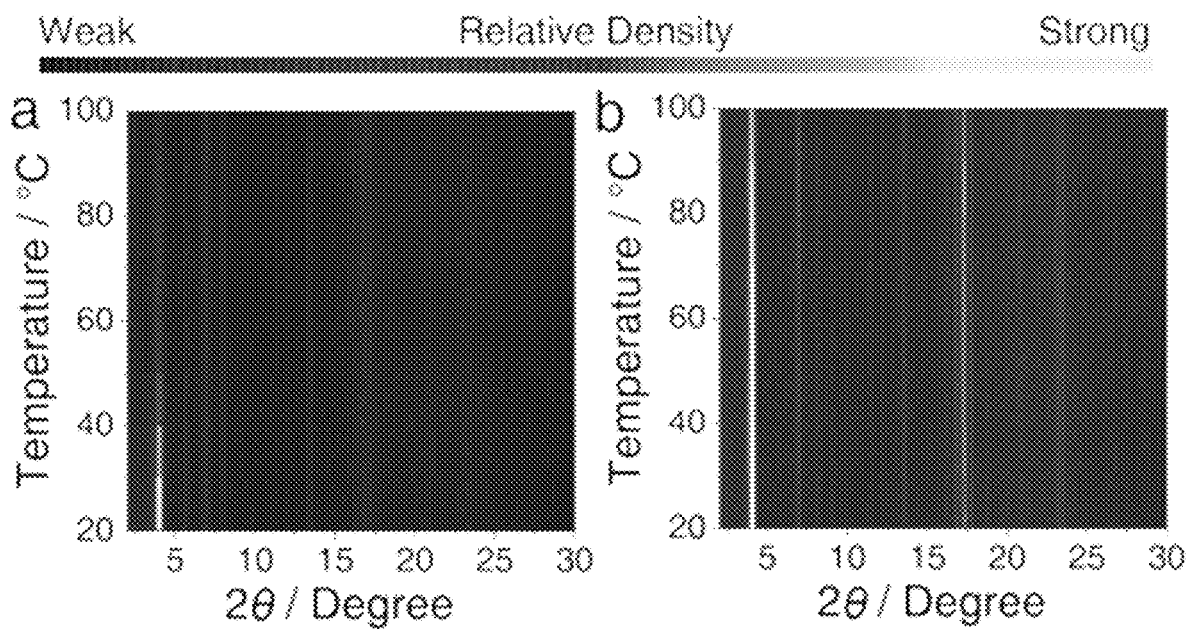
FIG. 6 provides a temperature-dependent PXRD pattern of CD-MOF-1 (left) and a temperature-dependent PXRD pattern of CD-HF-1 (right).

Temperature-dependent PXRD experiments were performed on both CD-HF-1 and CD-MOF-1 in order to assess the stability of these frameworks. A rapid loss of crystallinity in CD-MOF-1 was observed (FIG. 6) upon raising the temperature from 25° C. to 100° C., demonstrating that the solvent plays an important role in the stabilization of the crystalline structure of CD-MOF-1. In comparison, the PXRD experiments with CD-HF-1 show (FIG. 6) that this hybrid framework is stable after heating to 100° C., indicating that the hydrogen bonds in the frameworks improve the stability of the crystalline structure, suggesting that the solvent in CD-HF-1 is not as important for structural stabilization.

Figure 7:
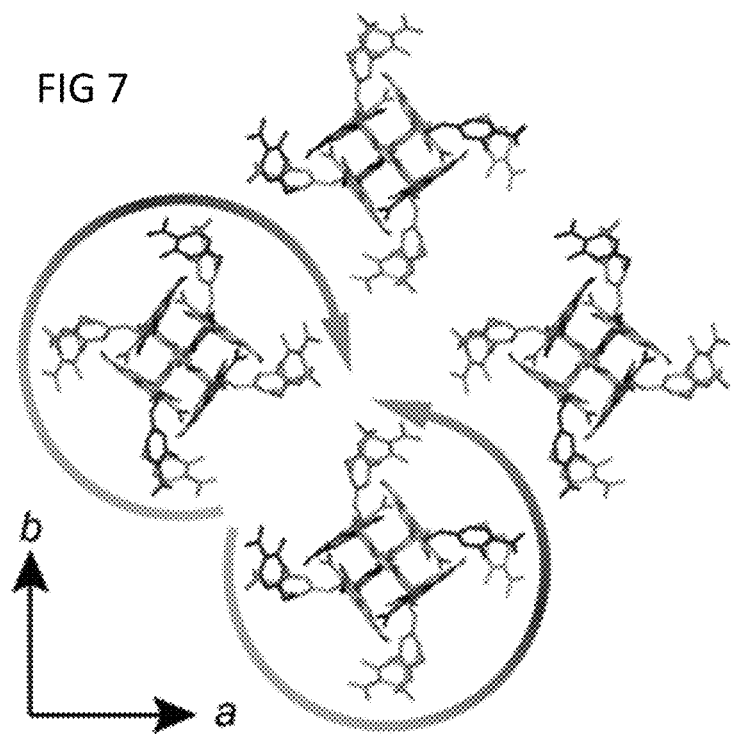
FIG. 7 provides a stick representation of the solid-state superstructure illustrating the handedness of helical arrangements of the achiral 4-MS-MS$^-$ anions along the c-axis, showing four packing units per turn.

In order to investigate the nature of the chirality present in the solid-state superstructure of CD-HF-1, the 4-MS-MS$^-$ anions in a single γ-CD dimer, parallel to a- or b-axes, were defined as one packing unit. By observing (FIG. 7) the multiple layers of anions down the c-axis, a helical arrangement of the achiral guest molecules, with four packing units per pitch, was observed. Each helix with a pitch of 61.3 Å has the opposite helicity to the adjacent one, which is consistent with the unit cell parameters of CD-HF-1. In supramolecular assembly processes, the induction and propagation[52-53] of chirality are usually considered to be some of the main factors that cause achiral molecules to pack in a chiral manner. In the case of CD-HF-1, the inherently chiral γ-CD building blocks most likely induce the chiral packing of the achiral 4-MS-MS$^-$ anions. Our observations suggest that the chiral packing of the counterions accounts for the lower symmetry of CD-HF-1 compared to that of CD-MOF-1.

Figure 3A:
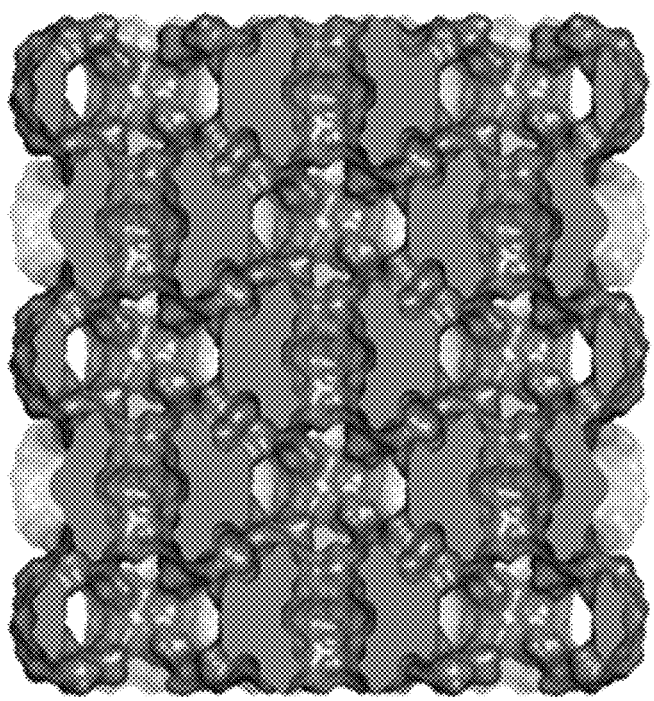
FIG. 3A shows a space-filling representation of sections of the porous superstructure of CD-MOF-1.
Figure 3B:
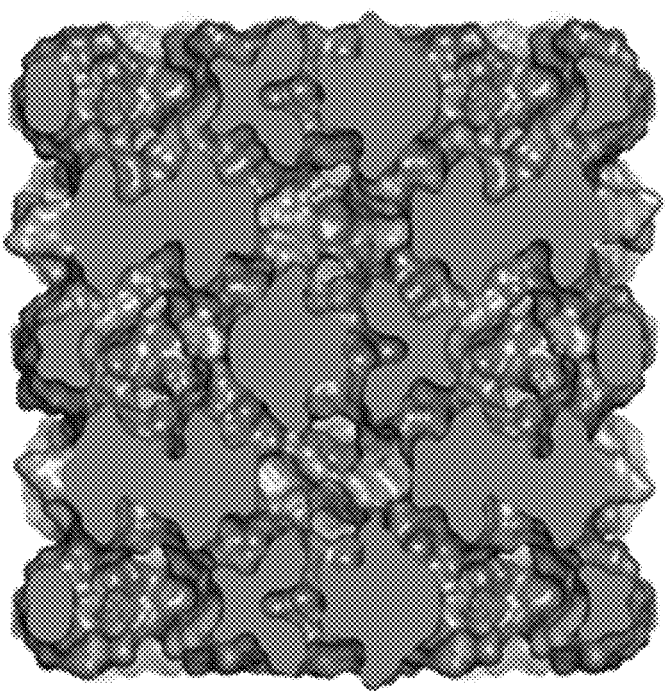
FIG. 3B provides a space-filling representation of sections of the porous superstructure of CD-HF-1, with γ-CD tori.

Next, we sought to investigate the porous structure of these hybrid frameworks, and to compare them with the porosity of CD-MOF-1. Space-filling representations of the pore channel sections of CD-MOF-1 and CD-HF-1 are shown in FIGS. 3A and 3B, respectively. The porous structure (FIG. 3A) of CD-MOF-1 consists of repeating (γ-CD)$_6$ cubic cavities with diameters of ~1.7 nm, and with two sets of channels connecting the contiguous cubes. One set of channels is comprised of the inner cavities of γ-CD tori, which propagate along the a-, b-, and c-axes, with windows that are ~0.78 nm in diameter. The second set of channels are located at the corners of the (γ-CD)$_6$ cubes with a minimal cross-section of 0.35 nm. In contrast, although CD-HF-1 has (FIG. 3B) the same arrangement of γ-CD cubes, significant differences were observed in the porosity of the framework, on account of the presence of the 4-MS-MS$^-$ anions. Approximately half of the volume of the (γ-CD)$_6$ cubic cavities is occupied by 4-MS-MS$^-$ anions, leaving the remaining volume available for other guest molecules. As in the case of CD-MOF-1, CD-HF-1 also possesses two sets of channels connecting the (γ-CD)$_6$ cubes. One set of channels, in common with CD-MOF-1, connects the inner cavities of the γ-CD tori. The channels along the c-axis are curtailed by the presence of the 4-MS-MS$^-$ anions, which occupy one side of the channel, serving as supramolecular baffles, and result in a change in the shape of the aperture from a circle to an oval, with a minimal cross-section of 0.33 nm. The channels in this set that lie along the a- and b-axes are blocked completely by the complex formed between each γ-CD dimer and three internalized 4-MS-MS$^-$ anions. As in the case of CD-MOF-1, the other set of channels are located at the corners of the cubes, but exhibit subtle differences as a consequence of deformations of the γ-CD tori in CD-HF-1

Figure 3C:
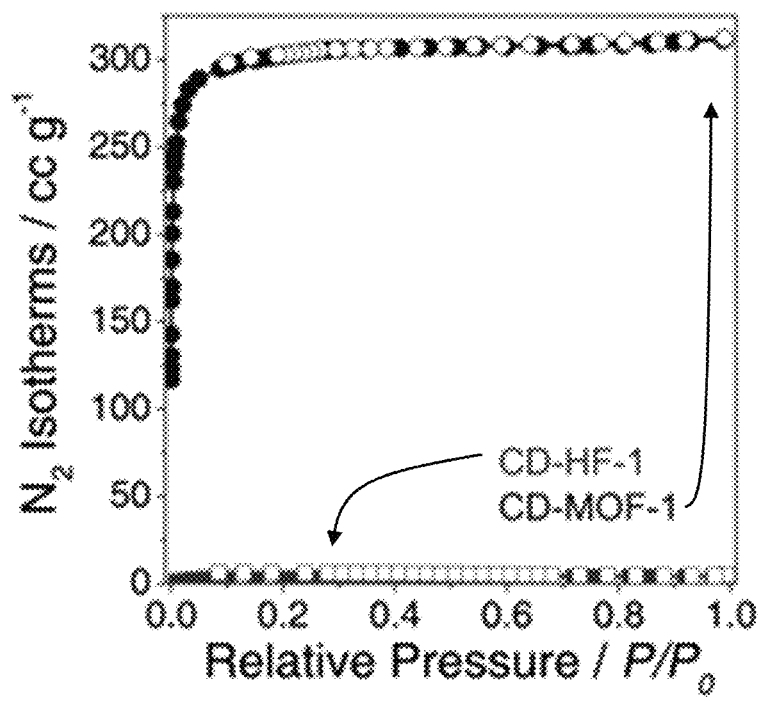
FIG. 3C provides a sorption isotherm measured on CD-MOF-1 and CD-HF-1 for $N_2$ at 77 K.
Figure 3D:
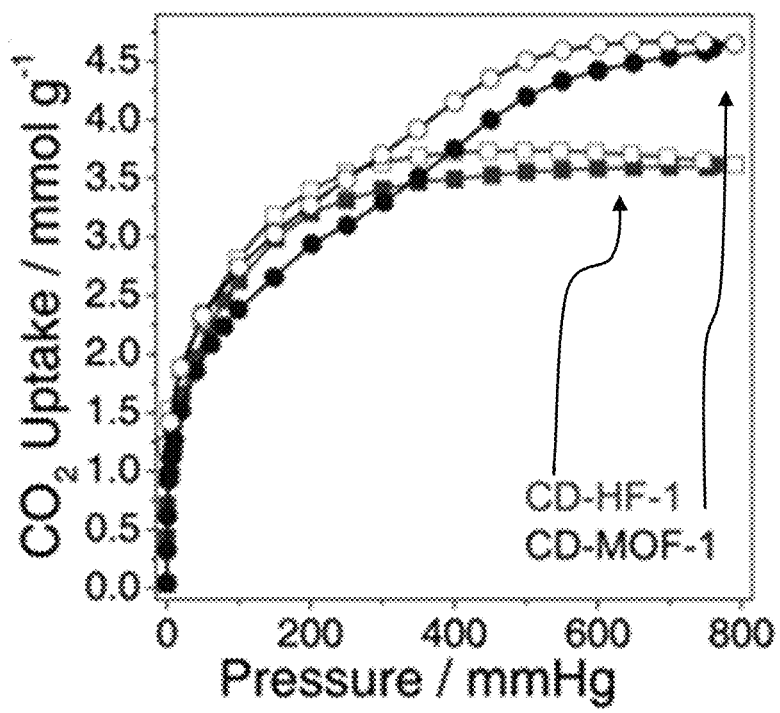
FIG. 3D provides a sorption isotherm measured on CD-MOF-1 and CD-HF-1 for $CO_2$ at 195 K.
Figure 8A:
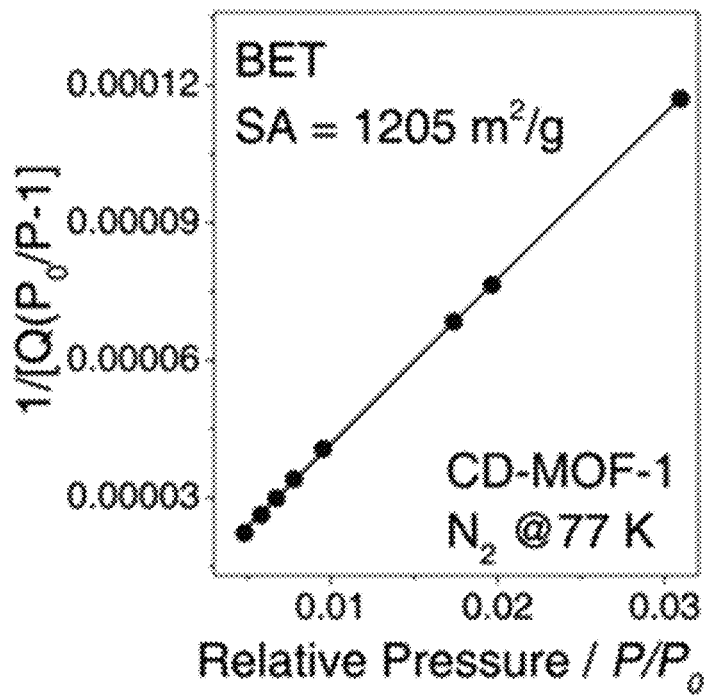
FIG. 8A provides a multi-point BET surface area plot of CD-MOF-1 based on $N_2$ sorption isotherms at 77 K.
Figure 8B:
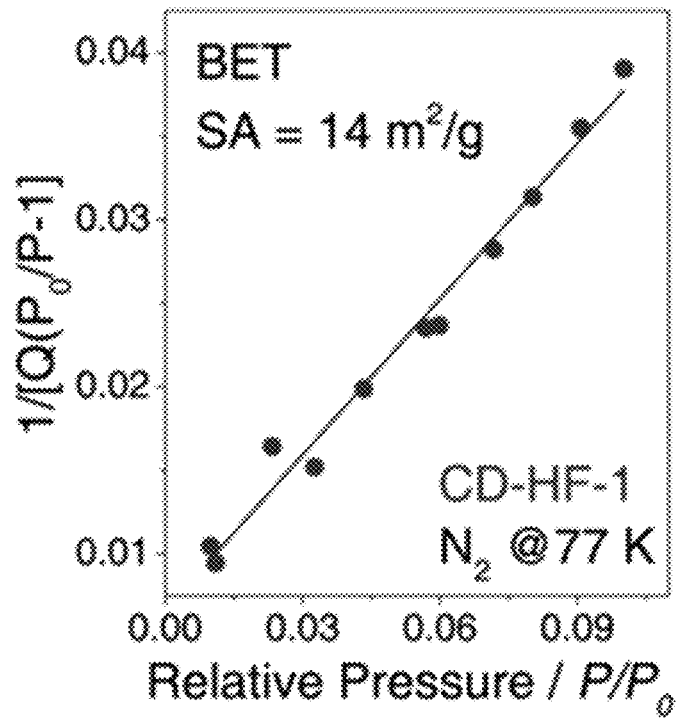
FIG. 8B provides a multi-point BET surface area plot of CD-HF-1 based on $N_2$ sorption isotherms at 77 K.
Figure 8C:
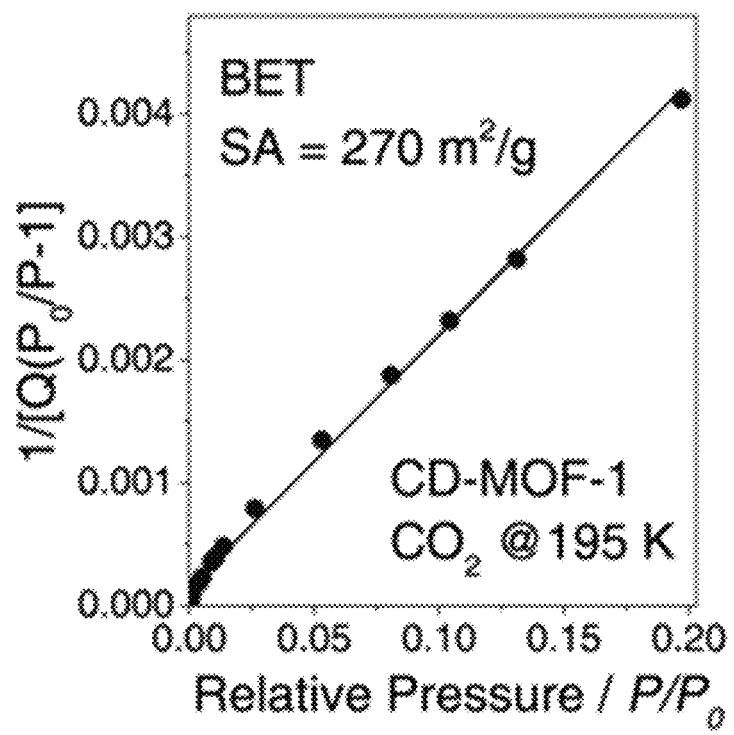
FIG. 8C shows a multi-point BET surface area plot of CD-MOF-1 based on $CO_2$ sorption isotherms at 195 K.
Figure 8D:
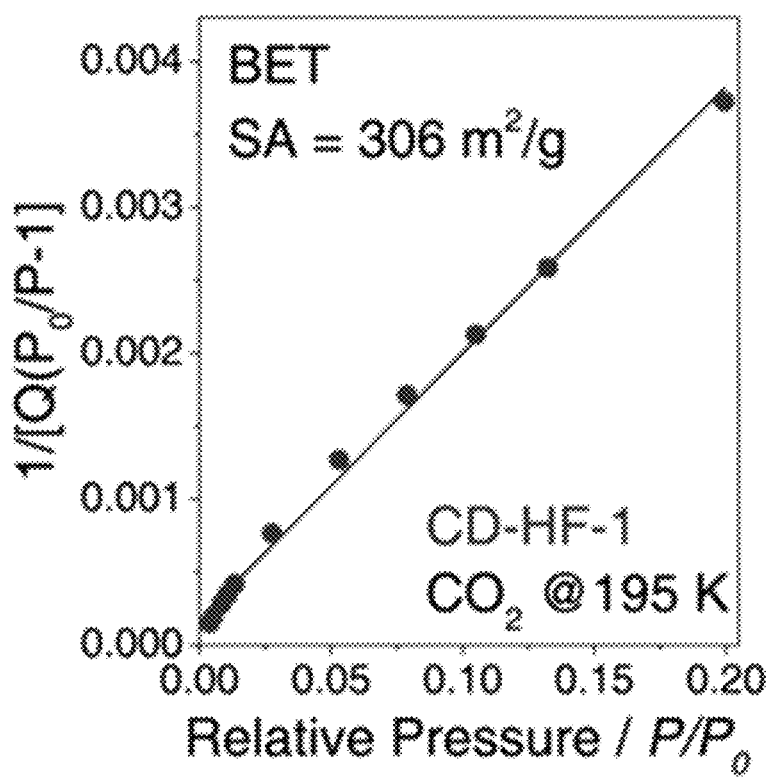
FIG. 8D shows a multi-point BET surface area plot of CD-HF-1 based on $CO_2$ sorption isotherms at 195 K.

Gas adsorption-desorption experiments were performed on both CD-HF-1 and CD-MOF-1 in order to investigate the differences in their permanent porosities. In comparison with CD-MOF-1, which displays (FIG. 3C) the type-I N$_2$ sorption isotherms, with the BET surface areas of 1205 m$^2$g 1 (FIG. 8A), CD-HF-1 does not uptake any N$_2$ gas molecules at 77 K (FIG. 8B). This observation is most likely a result of the size of the channels being comparable[54] with the kinetic size of N$_2$, a situation which hinders the diffusion of N$_2$ into the channels on account of the strong interactions[55] between the N$_2$ molecules and the apertures. In contrast, the CO$_2$ gas sorption isotherms of CD-HF-1 at 195 K indicate (FIG. 3D) an uptake of CO$_2$ that is higher than that of CD-MOF-1 at pressures below 300 mmHg. The BET surface area of 306 m$^2$g$^{-1}$ (FIG. 8D) compares favorably with the value of 270 m$^2$g 1 (FIG. 8C) for the BET surface area of CD-MOF-1, suggesting that the packing of the 4-MS-MS$^-$ anions in the crystal results in a reduction in the pore size distribution for CD-HF-1, and with a rough internal surface compared to that of CD-MOF-1. These observations indicate that CD-HF-1 is a hybrid ultramicroporous material, which can uptake gases selectively, with a higher surface area and different microporosity compared to that of CD-MOF-1.

Figure 4A:
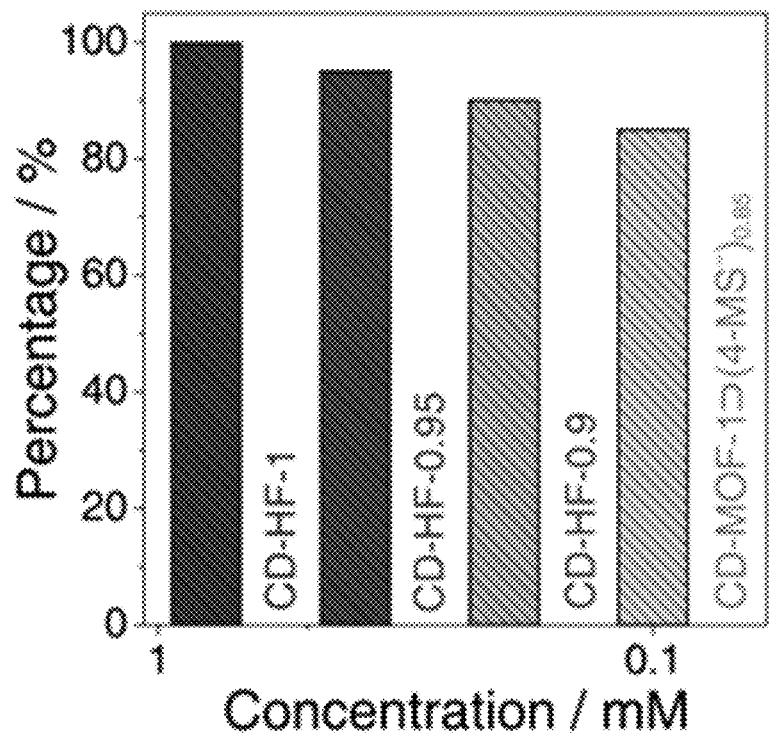
FIG. 4A provides a histogram of the percentages of total anions that are 4-MS-MS$^-$ anions in the crystal grown from the solution of 0.025 M γ-CD with 4-MS-MS$^-$ at different concentrations.
Figure 4B:
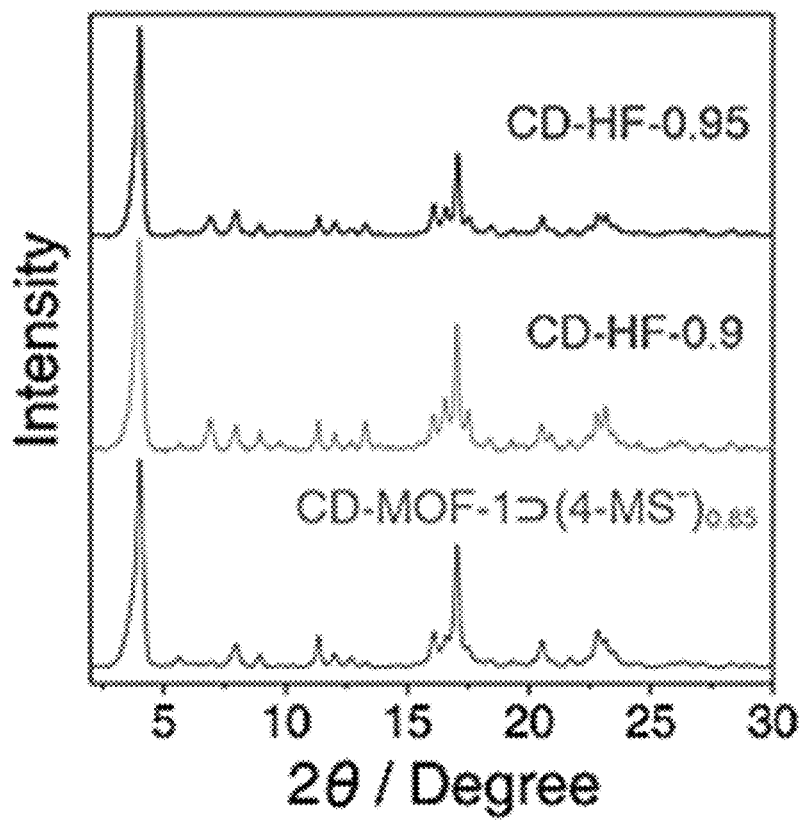
FIG. 4B provides powder X-ray diffraction of crystals, grown from a solution of 0.025 M γ-CD with 4-MS-MS$^-$ at different concentrations.
Figure 4C:
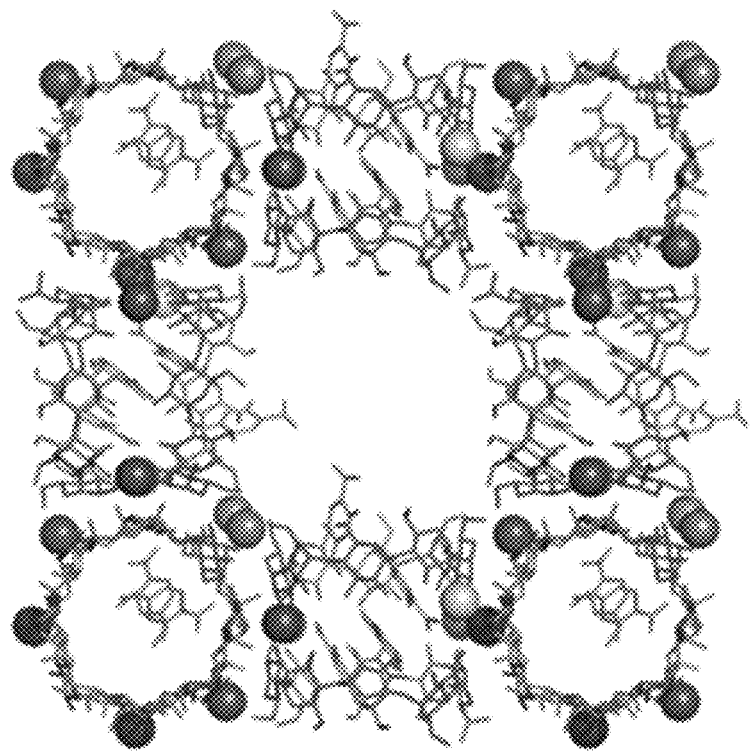
FIG. 4C shows a tubular representation of a slice through CD-HF-1, showing a single layer of γ-CD dimers, which was grown from a solution of 0.025 M γ-CD with 0.2M 4-MS$^-$.
Figure 4D:
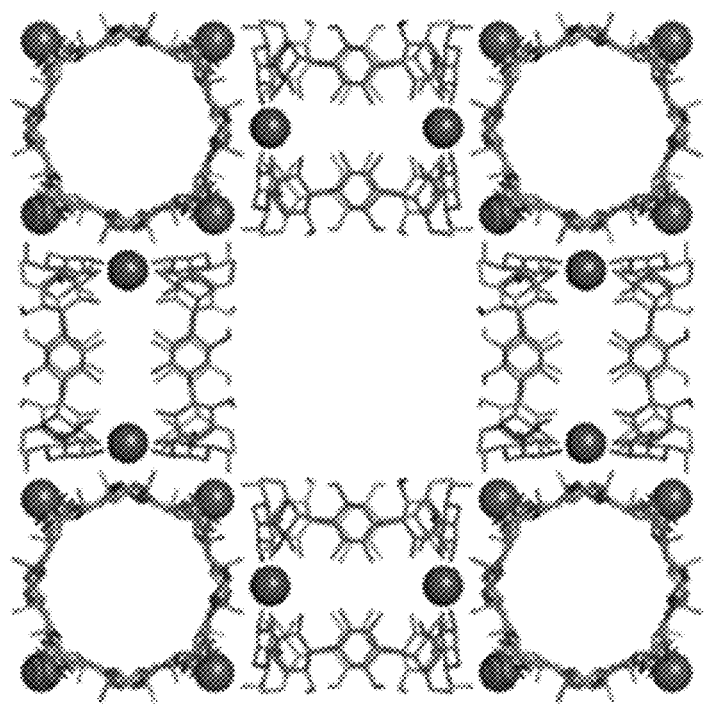
FIG. 4D shows a tubular representation of a slice through CD-HF-1, showing a single layer of γ-CD dimers, which was grown from a solution of 0.025 M γ-CD with 0.1 M 4-MS$^-$.

In order to gain a better understanding of the role of counteranions in the formation of the hybrid framework, solutions containing γ-CD (0.025 M) and varying concentrations of 4-MS anions (0.4 M and 0.2 M) were used in the growth of a selection of CD-HF crystals. These crystals were subsequently redissolved in D$_2$O and the ratios of 4-MS-MS$^-$ anions to γ-CD were analyzed (FIG. 4A) by 1H NMR spectroscopy. Crystals grown from the solution containing 0.4 M of 4-MS-MS$^-$ anions had a 4-MS$^-$:γ-CD ratio of 1.9:1, termed CD-HF-0.95, whereas those crystals grown from a 0.2 M solution of 4-MS-MS$^-$ anions had a 4-MS$^-$:γ-CD ratio of 1.8:1, designated CD-HF-0.9. These results suggest that OH anions participate in the charge balance of the cationic hybrid frameworks, by replacing the missing 4-MS-MS$^-$ anions as a result of their decreased concentration in the crystallization medium. The crystallographic information reveals that CD-HF-0.9 occupies the same cuboid space group P43212 as CD-HF-1, albeit with slight differences in the dimensions of the unit cell,[56] and exhibits the same packing arrangement of the γ-CD tori as CD-HF-1 with four, four, and two 4-MS-MS$^-$ anions being observed[57] in the γ-CD dimers parallel to a-, b-, and c-axes, respectively. Furthermore, hydrogen bonds are observed to link adjacent γ-CD building blocks, demonstrating hybrid frameworks similar to those in CD-HF-1. Unlike CD-HF-1, however, the half-occupied 4-MS-MS$^-$ anions in the (γ-CD)$_6$ cubic cavity cannot be located in the solid-state superstructure (FIG. 4C) of CD-HF-0.9, highlighting the fact that the ordered packing of organic anions inside the cavity of the (γ-CD)$_6$ cube, which do not form any hydrogen bonds to the framework, depends on the concentration of the 4-MS-MS$^-$ anion employed during the crystallization. Furthermore, the carboxyl groups of the two 4-MS-MS$^-$ anions inside the (γ-CD)$_6$ cavity of CD-HF-0.9 were observed with enhanced disorder compared to CD-HF-1, which probably results from an increase in free space inside the cavity of CD-HF-0.9. Importantly, the K$^+$ ion-pair that is 3.9 Å apart is often absent in the solid-state superstructure of CD-HF-0.9, with one K$^+$ ion occupying a six coordinate site, and the other occupying an eight coordinate site, on opposite sides of the (CD)$_6$ cube. When the concentration of 4-MS-MS$^-$ anions in solution was decreased to 0.1 M, at a ratio of 4:1 with respect to γ-CD, the resulting cubic crystals were found to contain 4-MS-MS$^-$ anions at a 4-MS$^-$:γ-CD ratio of 1.7:1, and occupied a cubic unit cell of space group I432, with a unit cell of approximately 31 Å3. We call this structure CD-MOF-1 ⊃ (4-MS)$_{0.85}$, which has the same solid-state structure as CD-MOF-1. In CD-MOF-1 ⊃ (4-MS)$_{0.85}$, none of the organic counteranions can be resolved in the crystal structure, suggesting the formation of a 'pure' MOF structure, with no contributions from the 4-MS-MS⁻ anions in the construction of the framework. These observations highlight the fact that the concentration-dependent chiral packing of organic anions, in this case 4-MS⁻, plays a role in the formation of CD-HFs that occupy the space group $P4_32_12$ on account of multiple interactions, including, anion-ligand, anion-cation, and anion-anion.

Although 4-MS-MS⁻ anions take part in the construction of CD-HF-1, the size of the inner channels of the γ-CD tori suggest the possibility of dynamic motion of these organic anions, as well as the channels being accessible to other inorganic anions. Anion exchange experiments were performed by immersing CD-HF-1 in a solution of KOH in MeOH.[58] ¹H NMR Spectroscopy revealed that the crystals lost 95% of their 4-MS-MS⁻ anions during the exchange process, which lasted seven days. Crystallographic analysis revealed a solid-state superstructure identical to that of CD-MOF-1, with a cubic unit cell of space group I432, indicating that a single-crystal to single-crystal transformation (FIG. 9) from CD-HF-1 to CD-MOF-1 occurred, facilitated by anion exchange. More importantly, the six-coordinate K⁺ ion-pairs in CD-HF-1 disappeared during the single-crystal to single-crystal transformation, after which only eight-coordinate K⁺ ions were observed. These K⁺ ions occupy the same positions as in CD-MOF-1, demonstrating a rearrangement of coordinated metal cations in the solid state, by taking advantage of the dynamic metal-ligand bonds present in these frameworks.

Figure 9:
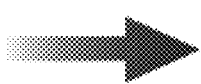
FIG. 9 illustrates the irreversible single-crystal to single-crystal transformation from CD-HF-1 in space group P43212, to CD-MOF-1 with space group I432, with a rearrangement of coordination K$^+$ cations by anion exchange of OH for 4-MS$^-$. The scheme also illustrates the reversible deformations of CD-MOF-1 as it switches between the space groups I432 and R32 when anion exchange is performed with OH and 4-methoxysalicylate.
Figure 9:
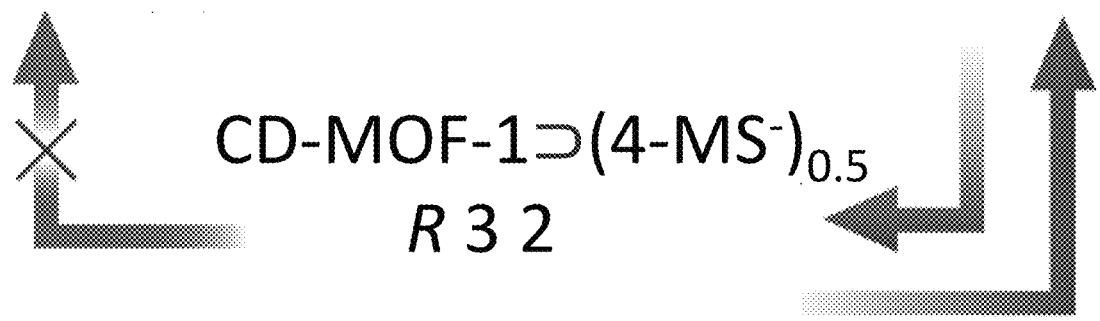

Having demonstrated that we could use anion exchange to transform CD-HF-1 into CD-MOF-1, we turned our attention to exploring the reversibility of this single-crystal to single-crystal transformation. Crystals of CD-MOF-1 were immersed in a solution of 4-MSK in MeOH and, following anion exchange, were redissolved in D₂O and analyzed by 1H NMR spectroscopy. This analysis revealed that the 4-MS-MS⁻ anion can be exchanged back into the channels of CD-MOF-1, but does not go above a 1:1 ratio with respect to γ-CD, even after 14 days. The crystals obtained, following this transformation, were found to occupy the trigonal group space $R^{32}$, which was observed[34-35] previously for CD-MOFs grown from γ-CD and potassium benzoate, thus demonstrating another distinct single-crystal to single-crystal transformation. We noted that some of the γ-CD tori are deformed in the crystal structure, suggesting a slow structural transformation. Furthermore, the CD-MOF-1 crystals in space group R32 were subjected (FIG. 9) to anion exchange using OH ions, which transforms the crystal back to the space group I432. All these observations indicate that the transformation of CD-MOF-1 between the I432 and R32 space groups is reversible, while the transformation of CD-HF-1 to CD-MOF-1 is irreversible (FIG. 9). This irreversibility can be attributed to the unique exploitation of three interactions synergistically to result in CD-HF-1: (i) the coordination of metal cations by organic ligands, (ii) intermolecular interactions between organic counteranions and organic ligands, and (iii) electrostatic interactions between metal cations and organic counteranions. The formation of CD-HF-1 can, therefore, be considered to be the result of a delicate balancing act between these three interactions during the crystallization process. Transformation to pure MOFs occurs by removing the intermolecular interactions between the organic counteranions and the organic ligands in the hybrid frameworks, with the irreversibility of this process being attributed to the generation of a more thermodynamically stable structure, on account of the rearrangement of K ions.

Materials and General Methods:

All reagents and solvents were purchased from commercial suppliers (Aldrich or Fisher) and were used without further purification. Solution 1H nuclear magnetic resonance (NMR) spectra were recorded on a Bruker Avance III 500 MHz spectrometers, with a working frequency of 500 MHz. Chemical shifts are reported in ppm relative to the signals corresponding to the residual non-deuterated solvents (D₂O: δH=4.79 ppm).

Powder X-ray diffraction (PXRD) patterns were collected at room temperature on a STOE-STADI MP powder diffractometer equipped with an asymmetric curved Germanium monochromator (CuKα1 radiation, λ=1.54056 Å) and one-dimensional silicon strip detector (MYTHEN2 1K from DECTRIS). The line focused Cu X-ray tube was operated at 40 kV and 40 mA. The activated powder was sandwiched between two Kapton foils and measured in transmission geometry in a rotating holder. Intensity data from 2 to 30 degrees two theta were collected over a period of 8 minutes. The instrument was calibrated against a NIST Silicon standard (640d) prior to the measurement.

A suitable crystal of CD-HFs and CD-MOFs was selected and the crystal was mounted on a MITIGEN holder with Paratone oil on a 'Bruker APEX-II CCD' diffractometer. The crystal was kept at 100.0 K during data collection. Using Olex2,[1] the structure was solved with the ShelXD[2] or ShelXT[3] structure solution program using direct methods and refined with the XL[2] refinement package using Least Squares minimization. The solvent masking procedure, as implemented in Olex[2], was used to remove the electronic contribution of solvent molecules from the refinement. As the exact solvent content is not known, only the atoms used in the refinement model are reported in the formula.

N₂ and CO₂ gases were used in all adsorption measurements. N₂ (77 K) isotherms were measured using a liquid N₂ bath (77 K). CO₂ (195 K) isotherms were measured using a mixture of dry ice and Me₂CO (195 K). Before the measurements, the CD-HFs or CD-MOFs were immersed in CH₂Cl₂ for three days, and then degassed at 45° C. for 12 h.[4] The Brunauer-Emmett-Teller (BET) surface areas were calculated from the adsorption data in the relative pressure (P/Po) ranging from 0 to 0.1.

Synthesis of CD-MOF-1

CD-MOF-1 was prepared by using a vapor diffusion approach according to the literature procedure,[4] except that a modified procedure was used as follows. γ-CD (6.5 mg, 5 µmol) and KOH (2.24 mg, 40 µmol) were dissolved in H₂O (0.2 mL). The solution was filtered through a 0.45-µm syringe filter and decanted into separate vials. MeOH (3 mL) was allowed to diffuse slowly into the solution over a period of a week. Colorless cubic crystals, were isolated, filtered, and washed with MeOH (3×1 mL). Dry CD-MOF-1 crystals suitable for X-ray diffraction and gas sorption analysis, were obtained by removing solvent in vacuum oven at 45° C.

Synthesis of CD-HFs

CD-MOFs with 4-methoxysalicylate (4 MS) anion were synthesized by vapor diffusion approach, with γ-CD as the organic ligand, potassium as the metal cation, and 4-methoxysalicylate as the counteranion. γ-CD (6.5 mg, 5 µmol) was dissolved in H₂O (0.2 mL) with potassium 4-methoxysalicylate (32.8 mg, 160 µmol). The solution was filtered through a 0.45-µm syringe filter and decanted into separate vials. MeOH (3 mL) was allowed to diffuse slowly into the solution over a period of 7 days. The resulting cubic crystals of CD-HF-1 were isolated, filtered and washed with MeOH (3×1 mL). CD-HF-0.95 and CD-HF-0.9 were grown with the same protocol from the solution of 0.025 M γ-CD with 0.4, and 0.2 M 4-methoxysalicylate, respectively. Dry crystals suitable for the recording of $^1$H NMR spectra, X-ray diffraction and gas sorption analysis, were obtained by removing solvent in a vacuum oven at 45° C.

Anion Exchange of CD-HFs and CD-MOFs

For anion exchange experiments, the as-synthesized CD-HF-1, obtained from the protocol described previously, was washed with MeOH (3×1 mL), and subsequently immersed in MeOH (1 mL) solution containing 2.24 mg (40 μmol) KOH. After allowing the solution to age for at least 7 days, crystals of CD-MOF-1-Exchanged were isolated, filtered, and washed with MeOH (3×1 mL), and the 1H NMR spectra was recorded after removing solvent in a vacuum oven at 45° C. For the reversible exchange experiment, the as-synthesiezed CD-MOF-1-Exchanged was immersed in MeOH (1 mL) solution containing 32.8 mg (160 μmol) 4-MSK for at least 14 days, resulting in crystals of CD-MOF-1⊃0.5-4 MS.

Crystallographic Refinement Details of CD-HF-1

Distance restraints were imposed on the disordered C55e, O41, O42 distances. The enhanced rigid-bond restraint (SHELX keyword RIGU) was applied on the disordered guest O41E >C56E and on some disordered oxygen atoms. (Acta Cryst. A68 (2012) 448-451 as was the SIMU restraint. The ISOR restraint were imposed on C56 C55A O41A atoms. Some water molecules were constrained.

Crystallographic Solvent Treatment Details of CD-HF-1

The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=14972.6 Å$^3$ [25.1%] Total electron count/cell=5740.4

Crystallographic Refinement Details of CD-HF-0.9

Distance restraints were imposed on the disordered oxygen atoms. The enhanced rigid-bond restraint (SHELX keyword RIGU) was applied (Acta Cryst. A68 (2012) 448-451) as well as restraints on similar amplitudes separated by less than 1.7 Ang. on O13s to C41s. The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell =19686.1 Å$^3$ [33.1%] Total electron count/cell =4810.7.

Crystallographic Solvent Treatment Details of CD-MOF-1⊃(4-MS$^-$)$_{0.85}$

The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=14248.7 Å$^3$ [47.8%] Total electron count/cell =5266.7

Crystallographic Refinement Details of CD-MOF-1⊃(4-MS$^-$)$_{0.5}$

The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell =20690.3 Å$^3$ [45.4%] Total electron count/cell =3037.2

Crystallographic Solvent Treatment Details of CD-MOF-1⊃(4-MS$^-$)$_{0.5}$

The enhanced rigid-bond restraint (SHELX keyword RIGU) was applied globally. (Acta Cryst. A68 (2012) 448-451). Distance restraints were imposed on some Carbon oxygen bonds to make them more reasonable with the disorder.

We claim:

1. A hybrid molecular framework comprising an ordered arrangement of cyclodextrin (CD), metal cations, and organic anions, wherein the organic anions are 4-methoxysalicylate (4-MS$^-$), wherein a first plurality of metal cations each have six coordination bonds and a second plurality of metal cations each have eight coordination bonds.

2. The framework of claim 1, wherein the CD is γ-CD.

3. The framework of claim 1, wherein the metal cations are K$^+$.

4. The framework of claim 1, wherein the CD is γ-CD and the metal cations are K$^+$ and wherein the molar ratio of the organic anions to CD is 2:1.

5. The framework of claim 1, wherein the framework comprises gas selective ultramicroporous apertures.

6. The framework of claim 1, wherein the organic anions are helically arranged.

7. The framework of claim 6, wherein the framework has a Brunauer-Emmett-Teller (BET) surface area of at least 300 m$^2$g$^{-1}$ for CO$_2$ gas sorption at 195 K.

8. The framework of claim 7, wherein the framework adsorbs CO$_2$ at 195 K and does not adsorb substantially N$_2$ at 77 K.

9. The framework of claim 1, wherein the framework exhibits body-centered cubic packing of (CD)$_6$ cubic units.

10. The framework of claim 1, wherein the framework exhibits a plurality of first CD-CD dimers parallel to a c-axis and wherein the framework has organic anions inside a cavity formed by the first CD-CD dimers.

11. The framework of claim 10, wherein the framework has two ipsilateral organic anions inside the cavity formed by the first CD-CD dimers.

12. The framework of claim 10, wherein the framework exhibits a plurality of second CD-CD dimers parallel to an a-axis or a b-axis and wherein the framework has organic anions inside a cavity formed by the second CD-CD dimers.

13. The framework of claim 12, wherein the framework has three organic anions inside the cavity formed by the second CD-CD dimers.

14. The framework of claim 1, wherein the framework has a molecular packing arrangement in the P 4$_3$ 2$_1$ 2 space group.

15. The framework of claim 14, wherein the framework has a 31×31×61.3 Å unit cell.

16. A method of preparing the hybrid molecular framework of claim 1, the method comprising preparing a solution comprising the CD, the metal cations, and the organic anions and crystalizing the framework.

17. The method of claim 16, wherein the molar ratio of the organic anions to CD in solution is at least 8.0:1.0.

18. The method of claim 16, wherein the CD is γ-CD and the metal cations are K$^+$.

19. A skin care product comprising the framework according to claim 1 and further comprising a skin lotion or a skin cream.

20. A method for whitening skin comprising contacting skin with the skin care product according to claim 19.

* * * * *